US012098166B2

(12) United States Patent
Mundt et al.

(10) Patent No.: US 12,098,166 B2
(45) Date of Patent: Sep. 24, 2024

(54) IMMUNOGENIC COMPOSITION AGAINST AVIAN INFLUENZA VIRUS H5 SUBTYPE

(71) Applicant: BOEHRINGER INGELHEIM VETMEDICA GMBH, Ingelheim am Rhein (DE)

(72) Inventors: Egbert Siegfried Mundt, Ingelheim am Rhein (DE); Xiaoping Cui, Shanghai (CN); Zenglei Hu, Shanghai (CN)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 692 days.

(21) Appl. No.: 17/291,924

(22) PCT Filed: Nov. 5, 2019

(86) PCT No.: PCT/CN2019/115471
§ 371 (c)(1),
(2) Date: May 6, 2021

(87) PCT Pub. No.: WO2020/093984
PCT Pub. Date: May 14, 2020

(65) Prior Publication Data
US 2022/0009970 A1    Jan. 13, 2022

(30) Foreign Application Priority Data

Nov. 6, 2018    (WO) ................ PCT/CN2018/114050

(51) Int. Cl.
| | | |
|---|---|---|
| *C07K 14/005* | (2006.01) | |
| *A61K 9/00* | (2006.01) | |
| *A61K 39/00* | (2006.01) | |
| *A61K 39/145* | (2006.01) | |
| *A61K 39/39* | (2006.01) | |
| *A61P 31/16* | (2006.01) | |
| *C12N 7/00* | (2006.01) | |
| *C12N 15/86* | (2006.01) | |
| *G01N 33/569* | (2006.01) | |

(52) U.S. Cl.
CPC .......... *C07K 14/005* (2013.01); *A61K 9/0019* (2013.01); *A61K 39/145* (2013.01); *A61K 39/39* (2013.01); *A61P 31/16* (2018.01); *C12N 7/00* (2013.01); *C12N 15/86* (2013.01); *G01N 33/56983* (2013.01); *A61K 2039/5252* (2013.01); *A61K 2039/54* (2013.01); *A61K 2039/545* (2013.01); *A61K 2039/552* (2013.01); *A61K 2039/55566* (2013.01); *C12N 2710/14043* (2013.01); *C12N 2760/16122* (2013.01); *C12N 2760/16134* (2013.01); *C12N 2760/16152* (2013.01); *C12N 2760/16163* (2013.01); *C12N 2760/16171* (2013.01); *G01N 2333/11* (2013.01); *G01N 2469/10* (2013.01)

(58) Field of Classification Search
CPC .... C07K 14/005; C07K 14/11; A61K 9/0019; A61K 39/145; A61K 39/39; A61K 2039/5252; A61K 2039/54; A61K 2039/545; A61K 2039/552; A61K 2039/55566; A61K 39/12; A61P 31/16; C12N 7/00; C12N 15/86; C12N 2710/14043; C12N 2760/16122; C12N 2760/16134; C12N 2760/16152; C12N 2760/16163; C12N 2760/16171; C12N 2015/8518; G01N 33/56983; G01N 2333/11; G01N 2469/10
See application file for complete search history.

(56) References Cited

U.S. PATENT DOCUMENTS

2010/0041740 A1    2/2010  Wong

FOREIGN PATENT DOCUMENTS

| JP | 1996333279 | | 2/1987 |
|---|---|---|---|
| JP | 1994505392 | | 6/1994 |
| JP | 2002541797 | A | 12/2002 |
| JP | 2010-508030 | A | 3/2010 |
| JP | 2010-523724 | A | 7/2010 |
| JP | 2015-512871 | A | 4/2015 |
| WO | 87/000862 | A1 | 2/1987 |
| WO | 92/15328 | A1 | 9/1992 |
| WO | 00/61736 | A2 | 10/2000 |
| WO | 2008052173 | A2 | 5/2008 |
| WO | 2008/128207 | A1 | 10/2008 |
| WO | 2013024113 | A1 | 2/2013 |
| WO | 2013/122827 | A1 | 8/2013 |

(Continued)

OTHER PUBLICATIONS

Webby, R.J., Weaver, E.A. (2015) "Centralized Consensus Hemagglutinin Genes Induce Protective Immunity against H1, H3, and H5 Influenze Viruses", PLOS ONE, 10(10): e0140702, doi:10.1371/journal.pone.0140702.

(Continued)

*Primary Examiner* — Nicole Kinsey White
*Assistant Examiner* — Samadhan Jaising Jadhao
(74) *Attorney, Agent, or Firm* — MINTZ, LEVIN, COHN, FERRIS, GLOVSKY AND POPEO, P.C.

(57) ABSTRACT

The invention relates to the field of veterinary medicine. The invention provides an immunogenic composition, comprising a hemagglutinin protein of avian influenza virus H5 subtype. Also provided is a method of differentiating animals naturally infected with AIV from animals vaccinated with the immunogenic composition of the invention. The immunogenic composition of the invention can provide a broader, more effective, long-lasting and early onset protection on poultry.

19 Claims, 2 Drawing Sheets

Specification includes a Sequence Listing.

(56) References Cited

FOREIGN PATENT DOCUMENTS

| WO | 2013/148164 A1 | 10/2013 |
| WO | 2015/099609 A1 | 7/2015 |
| WO | 2016/100926 A1 | 6/2016 |
| WO | 20170070620 A2 | 4/2017 |

OTHER PUBLICATIONS

Talazadeh, F. et al. (Jun. 1, 2014) "Evaluation of a commercial ELISA kit (IDEXX) to differentiate AI virus-infected poultry from AI-vaccinated poultry (DIVA)" Brazilian Journal of Poulty Science, Revista Brasileira De Ciência Avicola, 16(2), pp. 73-77, http://dx.doi.org/10.1590/1516-635x160273-78.

Chen, M.W., et al. "A consensus-hemagglutinin-based DNA vaccine that protects mice against divergent H5N1 influenza viruses", Proc. Natl. Acad. Sci. U.S.A. (2008), 105(36), pp. 13538-13543.

Pakula et. al. ((1989) "Genetic Analysis of Protein Stability and Function", Division of Biology, California Institute of Technology and Department of Biology, Massachusetts Institute of Technology, vol. 23, 289-310.

Donchenko A.S. et. al. (2009) "Development of a vaccine against the highly pathogenic H5N1 avian influenza virus", 22-26.

Philpott et al. (Jun. 1990) "Hemagglutinin Mutations Related to Attenuation and Altered Cell Tropism of a Virulent Avian Influenza A Virus", Journal of Virology, 64(6):2941-2947.

Lipatov et al. (Apr. 15, 2005) "Efficacy of H5 Influenza Vaccines Produced by Reverse Genetics in a Lethal Mouse Model", Journal of Infectious Diseases, 191(8):1216-1220.

Shinya et al. (Dec. 22, 2020) "Characterization of a Human H5N1 Influenza A Virus Isolated in 2003", Journal of Virology, 79(15):9926-9932.

Shinya et al. "Influenza A Virus (A/Hong Kong/213/2003(H5N1)) HA gene for hemagglutinin, complete cds, MDCK isolate, embryonated chicken egg isolate, Accession No. AB212054.1" NCBI-Genbank, Jan. 9, 2009 (Jan. 9, 2009), Features, Origin.

| Pool of all sequences (444) | Tier 1 consensus | Tier 2 (final) consensus |
|---|---|---|
| Clade 0 sequences (36) | → Consensus Clade 0 | |
| Clade 2.2 sequence (31) | → Consensus Clade 2.2 | |
| Clade 2.3.2 sequence (8) | → Consensus Clade 2.3.2 | |
| Clade 2.3.2.1 sequence (49) | → Consensus Clade 2.3.2.1 | |
| Clade 2.3.3 sequence (2) | → Consensus Clade 2.3.3 | |
| Clade 2.3.4 sequence (214) | → Consensus Clade 2.3.4 | |
| Clade 2.4 sequence (18) | → Consensus Clade 2.4 | H5Con1 |
| Clade 2.5 sequences (6) | → Consensus Clade 2.5 | |
| Clade 3 sequences (9) | → Consensus Clade 3 | |
| Clade 4 sequences (5) | → Consensus Clade 4 | |
| Clade 5 sequences (8) | → Consensus Clade 5 | |
| Clade 6 sequences (3) | → Consensus Clade 6 | |
| Clade 7 sequences (34) | → Consensus Clade 7 | |
| Clade 9 sequences (21) | → Consensus Clade 9 | |

Fig.1.

| Pool of all sequences (297) | Final consensus |
|---|---|
| Clade 2.3.2.1 sequence (49) | |
| Clade 2.3.4 sequence (214) | H5Con3 |
| Clade 7 sequences (34) | |

Fig. 2.

| Pool of all sequences (196) From years 2005-2012 | Final Consensus |
|---|---|
| Clade 2.2 sequence (31) | |
| Clade 2.3.2 sequence (2) | |
| Clade 2.3.2.1 sequence (47) | |
| Clade 2.3.4 sequence (80) | H5Con5 |
| Clade 7 sequences (34) | |
| Clade 1_2_8 like sequences (2) | |

Fig.3.

Fig 4

SEQUENCE LISTING

```
<160> NUMBER OF SEQ ID NOS: 11

<210> SEQ ID NO 1
<211> LENGTH: 551
<212> TYPE: PRT
<213> ORGANISM: Artificial Sequence
<220> FEATURE:
<223> OTHER INFORMATION: The amino acid sequence of the HA protein of
      strain duck/China/E319-2/03 but lacking the signal peptide of the
      amino terminus.

<400> SEQUENCE: 1

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Ser Ser Ser Phe Phe
    130                 135                 140

Arg Asn Val Val Trp Leu Ile Lys Lys Asn Asp Ala Tyr Pro Thr Ile
145                 150                 155                 160

Lys Arg Ser Tyr Asn Asn Thr Asn Gln Glu Asp Leu Leu Val Leu Trp
                165                 170                 175
```

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
            195                 200                 205

Leu Val Pro Lys Ile Ala Thr Arg Ser Lys Val Asn Gly Gln Ser Gly
            210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                    245                 250                 255

Val Lys Lys Gly Asp Ser Ala Ile Met Lys Ser Glu Val Glu Tyr Gly
                260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
            290                 295                 300

Tyr Val Lys Ser Asn Lys Leu Val Leu Ala Thr Gly Leu Arg Asn Ser
305                 310                 315                 320

Pro Gln Arg Glu Arg Arg Arg Lys Arg Gly Leu Phe Gly Ala Ile Ala
                        325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
            355                 360                 365

Ser Thr Gln Lys Ala Ile Asp Gly Val Thr Asn Lys Val Asn Ser Ile
            370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                    405                 410                 415

Phe Leu Asp Val Trp Thr Tyr Asn Ala Glu Leu Leu Val Leu Met Glu
                420                 425                 430

Asn Glu Arg Thr Leu Asp Phe His Asp Ser Asn Val Lys Asn Leu Tyr
            435                 440                 445

Asp Lys Val Arg Leu Gln Leu Arg Asp Asn Ala Lys Glu Leu Gly Asn
450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
            515                 520                 525

Ala Ile Met Val Ala Gly Leu Ser Leu Trp Met Cys Ser Asn Gly Ser
            530                 535                 540

Leu Gln Cys Arg Ile Cys Ile
545                 550

<210> SEQ ID NO 2
<211> LENGTH: 552
<212> TYPE: PRT
<213> ORGANISM: Artificial Sequence
<220> FEATURE:
<223> OTHER INFORMATION: The amino acid sequence of H5Con1 (without signal peptide)

<400> SEQUENCE: 2

Asp Gln Ile Cys Ile Gly Tyr His Ala Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Lys Ser Ser Phe Phe
130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550

<210> SEQ ID NO 3
<211> LENGTH: 568
<212> TYPE: PRT
<213> ORGANISM: Artificial Sequence
<220> FEATURE:
<223> OTHER INFORMATION: The amino acid sequence of H5Con3

<400> SEQUENCE: 3

Met Glu Lys Ile Val Leu Leu Leu Ala Ile Val Ser Leu Val Lys Ser
1               5                   10                  15

Asp

-continued

Asn Pro Thr Thr Tyr Ile Ser Val Gly Thr Ser Thr Leu Asn Gln Arg
        210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 4
<211> LENGTH: 567
<212> TYPE: PRT
<213> ORGANISM: Artificial Sequence
<220> FEATURE:
<223> OTHER INFORMATION: The amino acid sequence of H5Con5

<400> SEQUENCE: 4

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Asn Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
```

```
                420            425            430
Phe Leu Asp Val Trp Thr Tyr Asn Ala Glu Leu Leu Val Leu Met Glu
            435                440                445

Asn Glu Arg Thr Leu Asp Phe His Asp Ser Asn Val Lys Asn Leu Tyr
            450                455                460

Asp Lys Val Arg Leu Gln Leu Arg Asp Asn Ala Lys Glu Leu Gly Asn
465                470                475                480

Gly Cys Phe Glu Phe Tyr His Lys Cys Asp Asn Glu Cys Met Glu Ser
                485                490                495

Val Arg Asn Gly Thr Tyr Asp Tyr Pro Gln Tyr Ser Glu Glu Ala Arg
            500                505                510

Leu Lys Arg Glu Glu Ile Ser Gly Val Lys Leu Glu Ser Ile Gly Thr
            515                520                525

Tyr Gln Ile Leu Ser Ile Tyr Ser Thr Val Ala Ser Ser Leu Ala Leu
            530                535                540

Ala Ile Met Val Ala Gly Leu Ser Leu Trp Met Cys Ser Asn Gly Ser
545                550                555                560

Leu Gln Cys Arg Ile Cys Ile
            565
```

```
<210> SEQ ID NO 5
<211> LENGTH: 568
<212> TYPE: PRT
<213> ORGANISM: Artificial Sequence
<220> FEATURE:
<223> OTHER INFORMATION: The amino acid sequence of Con5Mut

<400> SEQUENCE: 5

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Asn Ser Trp Ser Asp His Glu Ala Ser
        130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
```

210                 215                 220
Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Val Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Gln Arg Glu Arg Arg Arg Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 6
<211> LENGTH: 241
<212> TYPE: PRT
<213> ORGANISM: Artificial Sequence
<220> FEATURE:
<223> OTHER INFORMATION: The amino acid sequence from position 60 to 300
      of H5Con5Mut

<400> SEQUENCE: 6

-continued

```
Leu Asp Gly Val Lys Pro Leu Ile Leu Arg Asp Cys Ser Val Ala Gly
1               5                   10                  15

Trp Leu Leu Gly Asn Pro Met Cys Asp Glu Phe Ile Asn Val Pro Glu
            20                  25                  30

Trp Ser Tyr Ile Val Glu Lys Ala Asn Pro Ala Asn Asp Leu Cys Tyr
        35                  40                  45

Pro Gly Asn Phe Asn Asp Tyr Glu Glu Leu Lys His Leu Leu Ser Arg
    50                  55                  60

Ile Asn His Phe Glu Lys Ile Gln Ile Ile Pro Lys Asn Ser Trp Ser
65                  70                  75                  80

Asp His Glu Ala Ser Ser Gly Val Ser Ser Ala Cys Pro Tyr Gln Gly
                85                  90                  95

Thr Pro Ser Phe Phe Arg Asn Val Val Trp Leu Ile Lys Lys Asn Asn
            100                 105                 110

Thr Tyr Pro Thr Ile Lys Arg Ser Tyr Asn Asn Thr Asn Gln Glu Asp
        115                 120                 125

Leu Leu Val Leu Trp Gly Ile His His Pro Asn Asp Ala Ala Glu Gln
    130                 135                 140

Thr Lys Leu Tyr Gln Asn Pro Thr Thr Tyr Ile Ser Val Gly Thr Ser
145                 150                 155                 160

Thr Leu Asn Gln Arg Leu Val Pro Lys Ile Ala Thr Arg Ser Lys Val
                165                 170                 175

Asn Gly Gln Asn Gly Arg Met Asp Phe Phe Trp Thr Ile Leu Lys Pro
            180                 185                 190

Asn Asp Ala Ile Asn Phe Glu Ser Asn Gly Asn Phe Ile Ala Pro Glu
        195                 200                 205

Tyr Ala Tyr Lys Ile Val Lys Lys Gly Asp Ser Ala Ile Met Lys Ser
    210                 215                 220

Glu Val Glu Tyr Gly Asn Cys Asn Thr Lys Cys Gln Thr Pro Ile Gly
225                 230                 235                 240

Ala
```

<210> SEQ ID NO 7
<211> LENGTH: 1707
<212> TYPE: DNA
<213> ORGANISM: Artificial Sequence
<220> FEATURE:
<223> OTHER INFORMATION: Optimized nucleic acid sequences of H5Con1

<400> SEQUENCE: 7

```
atggaaaaaa tcgtgctgct cttggctatt gtcagtttgg ttaagtcgga ccagatctgc      60
attggatacc acgccaacaa ctctaccgaa caagtcgaca ctatcatgga agaaacgtt      120 acagtgacgc acgctcagga tatcctggag aagacccata cggaaaact gtgtgacctc      180 gatggtgtga agcctttgat cctgcgtgac tgctctgtgg ctggttggct gctgggaaac      240
cctatgtgtg atgagttcat caacgtcccc gaatggtctt acattgttga aaggctaac      300 ccagccaacg acctctgcta cccgggtaac ttcaacgatt acgaggaatt gaagcacttg      360
ctgagtagga tcaaccattt cgaaaagatc cagatcatcc caaagtccag ctggtccgac      420
cacgaggctt cttcaggagt gagttcggcc tgtccgtacc agggcaagtc cagcttcttc      480
cgtaacgtgg tctggctgat taagaaaaac aacgcctacc aacaatcaa gaggtcatac      540 aacaacacga accaggaaga cctcttggtg ctgtggggta ccaccatcc aaacgatgct      600 gccgagcaga ctcgtctcta ccaaaacccg accacttaca tctccgtcgg caccagcact      660
```

-continued

```
ttgaaccaga gactggttcc gaagatcgca acacgctcca aagtgaacgg tcaaagcggc    720
aggatggact tcttctggac gatcctgaag cctaacgatg ctattaactt cgaatccaac    780
ggaaacttca tcgcacccga gtacgcgtac aagattgtca agaaaggtga ctctgcaatc    840
atgaaatcag agctggaata cggtaactgc aacacaaagt gtcaaacgcc catgggcgcg    900
atcaactctt caatgccttt ccacaacatc catcccctca caattggcga gtgccctaag    960
tacgttaaaa gtaacagact cgtgttggct accggattgc gtaactcgcc ccagagggaa   1020
cgccgtagga agaaacgcgg actgttcggt gctatcgccg gtttcattga gggtggctgg   1080
caaggcatgg tggacggctg gtacggatac caccatagta acgaacaggg atcgggttac   1140
gcagcggaca aggagtctac ccaaaaagct atcgatggtg tgactaacaa ggtcaactca   1200
atcattgaca aaatgaacac tcagttcgag gccgtcggca gagaattcaa caacctcgag   1260
agacgcatcg aaaacttgaa caagaaaatg gaagacggat tcctggatgt ctggacctac   1320
aacgctgagc tgctcgttct gatggagaac gaacgcactc tcgacttcca cgattccaac   1380
gtgaagaacc tctacgacaa agtcagactg caactccgcg ataacgctaa ggaattgggc   1440
aacggatgct tcgagttcta ccataagtgc gacaacgagt gtatggaatc cgtccgcaac   1500
ggcacatacg attacccaca gtacagcgag gaagctcgtc tcaagaggga ggaaatttct   1560
ggcgttaaat tggagtcaat cggaacatac caaatcctgt ccatttacag cacggttgca   1620
agttcgttgg cactggcgat catggtggcg ggcctcagct tgtggatgtg ctctaacgga   1680
tcactgcagt gccgcatctg tatttaa                                       1707
```

<210> SEQ ID NO 8
<211> LENGTH: 1707
<212> TYPE: DNA
<213> ORGANISM: Artificial Sequence
<220> FEATURE:
<223> OTHER INFORMATION: Optimized nucleic acid sequences of H5Con3

<400> SEQUENCE: 8

```
atggaaaaga tcgtgctgct cttggcaatt gtctccttgg ttaagagcga ccagatctgc     60
attggatacc acgcgaacaa cagcacagaa caagtcgaca cgatcatgga gaagaacgtt    120
acagtgacgc acgcacagga tatcctggag aaaacccata acggaaagct gtgtgacctc    180
gatggtgtga agcctttgat cctgcgcgac tgctctgtcg ctggttggct gctcggcaac    240
ccaatgtgtg atgagttcat caacgtcccg gaatggtcat acattgttga gaaggcaaac    300
cctgcgaacg acctctgcta ccccggtaac ttcaacgatt acgaggaatt gaagcacttg    360
ctgtctcgta tcaaccattt cgaaaagatc cagatcatcc caaagtccag ctggagtgac    420
cacgaggcat cgctgggagt gtcttcagcg tgtccttacc aaggtaaccc cagtttcttc    480
aggaacgtgg tctggctcat taagaaaaac aacacatacc cgacgatcaa gaaatcctac    540
aacaacacta accaggaaga cctcttggtg ctgtggggta tccaccatcc taacgatgag    600
gctgaacaga caaagctcta ccaaaacccc accacttaca tctctgtcgg cacctcaact    660
ttgaaccaga gactggttcc caaaatcgct acacgcagta aggtgaacgg tcaatcgggc    720
cgtatggact tcttctggac gatcctgaag ccaaacgatg ccattaactt cgaatccaac    780
ggaaacttca tcgctccgga gtacgcctac aaaattgtca agaaaggtga ctccgctatc    840
atgaagagcg aggttgaata cggtaactgc aacaccaaat gtcaaactcc aatcggcgcc    900
attaacagtt cgatgccatt ccacaacatc catccgctga caattggcga gtgccctaag    960
tacgttaaat ctaacaagct cgtgttggct accggattgc gtaactcacc ccagagggaa   1020
```
cgccgtagga agaaacgcgg actgttcggt gcaatcgcgg gtttcattga gggtggctgg 1080
caaggcatgg tggacggctg gtacggatac caccattcta acgaacaggg atcaggttac 1140
gctgccgaca aagagtccac ccaaaaggca atcgatggtg tgactaacaa agtcaacagc 1200
atcattgaca agatgaacac ccagttcgag gcggtcggca gagaattcaa caacctcgag 1260
agacgcatcg aaaacttgaa caagaaaatg gaagacggat tcctggatgt ctggacctac 1320
aacgctgagc tgctcgttct gatggagaac gaacgcactc tcgacttcca cgattcaaac 1380
gtgaaaaacc tctacgacaa ggtcagactg caactccgcg ataacgccaa ggaattgggc 1440
aacggatgct tcgagttcta ccataagtgc gacaacgagt gtatggaaag tgtgcgtaac 1500
ggcacttacg attacccccca gtactcggag gaagcccgtc tcaaaaggga ggaaatttcc 1560
ggcgtcaagt tggagagcat cggaacatac caaatcctgt ctatttactc aacggttgct 1620
tccagcttgg ctctggccat catggtggcc ggcctctcct tgtggatgtg cagtaacgga 1680
tcgctgcagt gcaggatctg tatttaa 1707

<210> SEQ ID NO 9
<211> LENGTH: 1707
<212> TYPE: DNA
<213> ORGANISM: Artificial Sequence
<220> FEATURE:
<223> OTHER INFORMATION: Optimized nucleic acid sequences of H5Con5

<400> SEQUENCE: 9
atggaaaaga tcgtgctgct cttggctatt gtctctctgg ttaaatcaga ccagatctgc 60
attggatacc acgccaacaa ctccacagaa caagtcgaca cgatcatgga gaagaacgtt 120
acagtgacgc acgctcagga tatcctcgag aaaacccata acggaaagct gtgtgacctc 180
gatggtgtga agcctttgat cctgagggac tgcagtgtcg ccggttggct gctcggcaac 240
ccaatgtgtg atgagttcat caacgtcccg gaatggtcct acattgttga gaaggctaac 300
cctgccaacg acctctgcta ccccggtaac ttcaacgatt acgaggaatt gaagcacttg 360
ctgtctagaa tcaaccattt cgaaaagatc cagatcatcc caaagtccag ctggtcagac 420
cacgaggctt cttcaggagt gagttcggcc tgtccttacc aaggtactcc cagcttcttc 480
aggaacgtgg tctggctgat taagaaaaac aacacatacc cgacgatcaa gagatcttac 540
aacaacacta accaggaaga cctcttggtg ctgtggggta tccaccatcc taacgatgct 600
gccgagcaga caaagctcta ccaaaacccc accacttaca tcagtgtcgg cacctcgact 660
ttgaaccagc gcctggttcc caaaatcgca acacgtagta aggtgaacgg tcaatcgggc 720
aggatggact tcttctggac gatcctcaag ccaaacgatg ctattaactt cgaaagcaac 780
ggaaacttca tcgcaccgga gtacgcgtac aaaattgtca agaaaggtga ctccgcaatc 840
atgaagagcg aggttgaata cggtaactgc aacaccaaat gtcaaactcc aatcggcgcg 900
attaactcca gcatgccatt ccacaacatc catccgctga caattggcga gtgccctaag 960
tacgttaaat ctaacaagct cgtgttggcc accggattga ggaactcacc ccagagagaa 1020
cgccgtagga gaaagcgcgg actgttcggt gctatcgccg gtttcattga gggtggctgg 1080
caaggcatgg tggacggctg gtacggatac caccattcta acgaacaggg atcaggttac 1140
gcagcggaca aagagtccac ccaaaaggct atcgatggtg tgactaacaa agtcaacagc 1200
atcattgaca agatgaacac ccagttcgag gccgtcggcc gcgaattcaa caacctcgag 1260
cgccgtatcg aaaacttgaa caagaaaatg gaagacggat tcctggatgt ctggacctac 1320

```
aacgctgagc tgctcgttct gatggagaac gaacgtactc tcgacttcca cgattcaaac    1380
gtgaaaaacc tctacgacaa ggtccgcctg caactccgtg ataacgctaa ggaattgggc    1440
aacggatgct tcgagttcta ccataagtgc gacaacgagt gtatggaaag tgtgcgcaac    1500
ggcacttacg attacccca gtactcggag aagctaggt tgaaaagaga ggaaatttcc      1560
ggcgtcaagt tggagagcat cggaacatac caaatcctga gtatttactc gacggttgca    1620
tcttcattgg cactggcgat catggtggcg ggcctctcct tgtggatgtg ctccaacgga    1680
agcctgcagt gccgtatctg tatttaa                                        1707
```

<210> SEQ ID NO 10
<211> LENGTH: 1704
<212> TYPE: DNA
<213> ORGANISM: Artificial Sequence
<220> FEATURE:
<223> OTHER INFORMATION: Optimized nucleic acid sequence of H5ConMut

<400> SEQUENCE: 10

```
atggaaaaga tcgtgctgct cttggctatt gtctctctgg ttaaatcaga ccagatctgc     60
attggatacc acgccaacaa ctccacagaa caagtcgaca cgatcatgga gaagaacgtt    120
acagtgacgc acgctcagga tatcctcgag aaaacccata cggaaagct gtgtgacctc    180 gatggtgtga agcctttgat cctgagggac tgcagtgtcg ccggttggct gctcggcaac    240
ccaatgtgtg atgagttcat caacgtcccg gaatggtcct acattgttga aaggctaac    300 cctgccaacg acctctgcta ccccggtaac ttcaacgatt acgaggaatt gaagcacttg    360
ctgtctagaa tcaaccattt cgaaaagatc cagatcatcc caagaataga ctggtcagac    420
cacgaggctt cttcaggagt gagttcggcc tgtccttacc aaggtactcc cagcttcttc    480
aggaacgtgg tctggctgat taagaaaac aacacatacc cgacgatcaa gagatcttac    540
aacaacacta accaggaaga cctcttggtg ctgtggggta tccaccatcc taacgatgct    600
gccgagcaga caaagctcta ccaaaacccc accacttaca tcagtgtcgg cacctcgact    660
ttgaaccagc gcctggttcc caaaatcgca cacgtagta aggtgaacgg tcaaaatggc    720
aggatggact tcttctggac gatcctcaag ccaaacgatg ctattaactt cgaaagcaac    780
ggaaacttca tcgcaccgga gtacgcgtac aaaattgtca gaaaggtga ctccgcaatc    840 atgaagagcg aggttgaata cggtaactgc aacaccaaat gtcaaactcc aatcggcgcg    900
attaactcca gcatgccatt ccacaacatc catccgctga caattggcga gtgccctaag    960
tacgttaaat ctaacaagct cgtgttggcc accggattga ggaactcacc cagagagaa    1020 cgccgtagga gaaagcgcgg actgttcggt gctatcgccg gtttcattga gggtggctgg    1080
caaggcatgg tggacggctg gtacggatac accattcta acgaacaggg atcaggttac    1140
gcagcggaca aagagtccac ccaaaaggct atcgatggtg tgactaacaa agtcaacagc    1200
atcattgaca gatgaacac ccagttcgag gccgtcggcc gcgaattcaa caacctcgag    1260
cgccgtatcg aaaacttgaa caagaaaatg gaagacggat tcctggatgt ctggacctac    1320
aacgctgagc tgctcgttct gatggagaac gaacgtactc tcgacttcca cgattcaaac    1380
gtgaaaaacc tctacgacaa ggtccgcctg caactccgtg ataacgctaa ggaattgggc    1440
aacggatgct tcgagttcta ccataagtgc gacaacgagt gtatggaaag tgtgcgcaac    1500
ggcacttacg attacccca gtactcggag aagctaggt tgaaaagaga ggaaatttcc      1560
ggcgtcaagt tggagagcat cggaacatac caaatcctga gtatttactc gacggttgca    1620
tcttcattgg cactggcgat catggtggcg ggcctctcct tgtggatgtg ctccaacgga    1680
```

```
agcctgcagt gccgtatctg tatt                                           1704

<210> SEQ ID NO 11
<211> LENGTH: 723
<212> TYPE: DNA
<213> ORGANISM: Artificial Sequence
<220> FEATURE:
<223> OTHER INFORMATION: Optimized nucleic acid sequence encoding the
      amino acid sequence from position 60 to 300 of H5Con5Mut

<400> SEQUENCE: 11
ctcgatggtg tgaagccttt gatcctgagg gactgcagtg tcgccggttg gctgctcggc    60
aacccaatgt gtgatgagtt catcaacgtc ccggaatggt cctacattgt tgagaaggct    120
aaccctgcca acgacctctg ctaccccggt aacttcaacg attacgagga attgaagcac    180
ttgctgtcta gaatcaacca tttcgaaaag atccagatca tcccaaagaa tagctggtca    240
gaccacgagg cttcttcagg agtgagttcg gcctgtcctt accaaggtac tcccagcttc    300
ttcaggaacg tggtctggct gattaagaaa acaacacat acccgacgat caagagatct    360
tacaacaaca ctaaccagga agacctcttg gtgctgtggg gtatccacca tcctaacgat    420
gctgccgagc agacaaagct ctaccaaaac cccaccactt acatcagtgt cggcacctcg    480
actttgaacc agcgcctggt tcccaaaatc gcaacacgta gtaaggtgaa cggtcaaaat    540
ggcaggatgg acttcttctg gacgatcctc aagccaaacg atgctattaa cttcgaaagc    600
aacggaaact tcatcgcacc ggagtacgcg tacaaaattg tcaagaaagg tgactccgca    660
atcatgaaga gcgaggttga atacggtaac tgcaacacca aatgtcaaac tccaatcggc    720
gcg                                                                  723
```

IMMUNOGENIC COMPOSITION AGAINST AVIAN INFLUENZA VIRUS H5 SUBTYPE

CROSS REFERENCE TO RELATED APPLICATIONS

This application is a national stage application filed under 35 U.S.C. § 371, of International Patent Application No. PCT/CN2019/115471, filed on Nov. 5, 2019, entitled IMMUNOGENIC COMPOSITION AGAINST AVIAN INFLUENZA VIRUS H5 SUBTYPE; which claims the benefit of and priority to PCT Application No. PCT/CN2018/114050, filed on Nov. 6, 2018, each of which is hereby incorporated by reference in its entirety.

FIELD OF THE INVENTION

The invention relates to the field of veterinary medicine, in particular to an immunogenic composition against avian influenza virus H5 subtype.

BACKGROUND OF THE INVENTION

Avian influenza virus (AIV) belongs to the type of influenza A viruses, and it occurs naturally among wild aquatic birds worldwide and can infect domestic poultry and other birds including mammals. Influenza A viruses are divided into subtypes on the basis of two proteins on the surface of the virus: hemagglutinin (HA) and neuraminidase (NA). There are 18 known HA subtypes and 11 known NA subtypes. Many different combinations of HA and NA proteins are possible. For example, an "H5N1 virus" means that the virus has an HA subtype 5 and an NA subtype 1.

There are nine known subtypes of H5 viruses (H5N1, H5N2, H5N3, H5N4, H5N5, H5N6, H5N7, H5N8, and H5N9, herein referred as "H5Nx"). Most H5 viruses identified worldwide in wild birds and poultry are low pathogenicity avian influenza virus, but some H5 containing viruses belong to highly pathogenic avian influenza (HPAI) viruses. H5Nx viruses evolve rapidly and result in considerable divergent antigenic variation among different clades that reveal evolutionary relationships among different H5 lineages. Infection of poultry with HPAI viruses can cause severe diseases with high mortality.

For the countries with endemic H5Nx virus, vaccination has been used to control the disease. The most common AIV vaccines are vaccines containing inactivated whole virus (inactivated vaccines) which are prepared by the inactivation of a whole virus and the emulsification with proper adjuvants. However, the inactivated vaccine cannot provide a broad protection against different clades. Due to the rapid evolution of AIV, people have to continually develop new vaccines against different clades. Moreover, the production of the inactivated vaccine requires a large amount of live AIV, and thus the biosafety is a serious problem.

HA protein is the receptor-binding and membrane fusion glycoprotein of influenza A virus. HA protein has been known to be capable of eliciting protective antibodies, and thus researchers become interested in the development of subunit vaccines based on the recombinant HA protein. WO2007/019094 discloses an HA molecule comprising an amino acid substitution in the receptor binding site that makes the HA molecule more antigenic compared with the HA molecule lacking the amino acid substitution in its receptor binding site. WO2008/052173 discloses a hemagglutinin protein of avian influenza virus H5 subtype (hereinafter referred to as "HA protein of AIV H5 subtype" or "H5 HA protein") comprising some amino acid mutations, and the vaccines comprising the adjuvanted H5 HA protein can provide the protection from clinical disease caused by influenza A virus. However, the above disclosures are not related to broader protection on influenza A viruses of different clades.

WO2013/148164 discloses a method for the generation of optimized H5N1 and H1N1 influenza HA polypeptide based on human H5N1 and swine H1N1 influenza isolates. An influenza virus-like particle (VLP) comprising the optimized influenza HA polypeptide is also prepared. The experimental results show that the VLP can elicit an antibody response that can recognize influenza viruses of two different clades in mice, but the protection efficacy is only 40-60%.

There is a need to develop a vaccine which can provide a broader, more effective, long-lasting and early onset protection on poultry against AIV H5 subtype.

SUMMARY OF THE INVENTION

The invention provides an immunogenic composition, comprising a hemagglutinin protein of avian influenza virus H5 subtype, wherein the hemagglutinin protein comprises: (a) amino acid residues 120N or 120S, 155N, and 223N or 223S; and (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I; with numbering with reference to amino acid residues as set forth in SEQ ID NO:1.

The invention also provides a method of preparing an immunogenic composition, comprising: (i) culturing cells containing an expression vector expressing a hemagglutinin protein of avian influenza virus H5 subtype; and (ii) harvesting the whole cell culture; wherein the hemagglutinin protein comprises: (a) amino acid residues 120N or 120S, 155N, and 223N or 223S; and (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I; with numbering with reference to amino acid residues as set forth in SEQ ID NO:1.

Also provided is an immunogenic composition of the invention, for use in the prevention and/or treatment of infections caused by an avian influenza virus, preferably by H5Nx. In one embodiment, H5Nx is H5N1, H5N2 and/or H5N6. In one embodiment, H5Nx is H5N1. In one embodiment, H5Nx is H5N2. In one embodiment, H5Nx is H5N6. In one embodiment, H5Nx is H5N1 and H5N2. In one embodiment, H5Nx is H5N2 and H5N6.

Also provided is a method of differentiating animals naturally infected with AIV from animals vaccinated with the immunogenic composition of the invention.

The immunogenic composition of the invention can provide a broader, more effective, long-lasting and early onset protection on poultry. In one embodiment, the immunogenic composition of the invention provides a broader protection on poultry. In one embodiment, the immunogenic composition of the invention provides more effective protection on poultry. In one embodiment, the immunogenic composition of the invention provides long-lasting protection on poultry. In one embodiment, the immunogenic composition of the invention provides early onset protection on poultry.

DETAILED DESCRIPTION OF THE INVENTION

In one aspect, the invention provides an immunogenic composition, comprising a H5 HA protein, wherein the H5

HA protein comprises: (a) amino acid residues 120N or 120S, 155N, and 223N or 223S; and (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I; with numbering with reference to amino acid residues as set forth in SEQ ID NO:1.

As used herein, the term "immunogenic composition", also named as "vaccine", refers to a composition that comprises at least one antigen which elicits an immune response to the composition. The host will display either a therapeutic or protective immune response such that resistance to new infections will be enhanced and/or the severity of clinical signs is reduced.

The amino acid sequence of the H5 HA protein is designed through a series of HA amino acid sequence alignments, the subsequent generation of consensus amino acid sequences and the analysis of the most common residue at each position. As used herein, the terms "hemagglutinin protein of the invention", "HA protein of AIV H5 subtype" and "H5 HA protein" are interchangeable.

As used herein, SEQ ID NO:1 represents the amino acid sequence of the HA protein of strain A/duck/China/E319-2/03 but lacking the signal peptide of the amino terminus (the amino acid sequence of the HA protein of strain A/duck/China/E319-2/03 was also published in WO2008/052173). SEQ ID NO:1 is used as a standard sequence of the HA protein for determining the amino acid position of the HA protein of the invention.

The numbering of the amino acid positions of HA protein of the invention as used herein refers to the amino acid position as set forth in SEQ ID NO:1. For example, the designation "120N or 120S" means N or S at a position corresponding to position 120 of SEQ ID NO:1. The "155N" means N at a position corresponding to position 155 of SEQ ID NO:1. The "223N or 223S" means N or S at a position corresponding to position 223 of SEQ ID NO:1. The "61D" means D at a position corresponding to position 61 of SEQ ID NO:1. The "87I" means I at a position corresponding to position 87 of SEQ ID NO:1. The "99A" means A at a position corresponding to position 99 of SEQ ID NO:1. The "102A" means A at a position corresponding to position 102 of SEQ ID NO:1. The "110N" means N at a position corresponding to position 110 of SEQ ID NO:1. The "136S" means S at a position corresponding to position 136 of SEQ ID NO:1. The "140D" means D at a position corresponding to position 140 of SEQ ID NO:1. The "149S" means S at a position corresponding to position 149 of SEQ ID NO:1. The "156T" means T at a position corresponding to position 156 of SEQ ID NO:1. The "157P" means P at a position corresponding to position 157 of SEQ ID NO:1. The "170N" means N at a position corresponding to position 170 of SEQ ID NO:1. The "172T" means T at a position corresponding to position 172 of SEQ ID NO:1. The "178R" means R at a position corresponding to position 178 of SEQ ID NO:1. The "190V" means V at a position corresponding to position 190 of SEQ ID NO:1. The "191L" means L at a position corresponding to position 191 of SEQ ID NO:1. The "200A" means A at a position corresponding to position 200 of SEQ ID NO:1. The "226V" means V at a position corresponding to position 226 of SEQ ID NO:1. The "243D" means D at a position corresponding to position 243 of SEQ ID NO:1. The "268Y" means Y at a position corresponding to position 268 of SEQ ID NO:1. The "279A" means A at a position corresponding to position 279 of SEQ ID NO:1. The "298I" means I at a position corresponding to position 298 of SEQ ID NO:1. The methods for the determining the positions of amino acids are known in the art, including but not limited to amino acid alignment performed by using BLAST Program.

In one embodiment of the immunogenic composition of the invention, the H5 HA protein comprises any one of the amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I. In one embodiment, the H5 HA protein of the invention comprises two amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I. In one embodiment, the H5 HA protein of the invention comprises three, four, five, . . . , or all of the amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I. The entire HA protein from a naturally occurring AIV is about 568 amino acid residues in length, and all amino acid residues upstream of amino acid 514 are located on the viral surface. The above amino acid sites of the invention are identified as being located within the region of amino acid 60-300 of the HA protein which is believed to comprise most of the immunogenic epitopes. In one embodiment, the H5 HA protein of the invention further comprises amino acid residues 120N or 120S, 155N, and 223N or 223S. In one embodiment, the H5 HA protein of the invention comprises amino acid residues 120N, 155N, and 223N. In one embodiment, the H5 HA protein of the invention comprises amino acid residues 120N, 155N, and 223S. In one embodiment, the H5 HA protein of the invention comprises amino acid residues 120S, 155N, and 223N. In one embodiment, the H5 HA protein of the invention comprises amino acid residues 120S, 155N, and 223S.

In one embodiment of the immunogenic composition of the invention, the H5 HA protein comprises amino acid residues 61D, 87I, 99A, 102A, 110N, 120N, 136S, 140D, 149S, 155N, 156T, 157P, 170N, 172T, 178R, 190V, 191L, 200A, 223N, 226V, 243D, 268Y, 279A and 298I. In one embodiment, the H5 HA protein of the invention comprises amino acid residues 61D, 87I, 99A, 102A, 110N, 120S, 136S, 140D, 149S, 155N, 156T, 157P, 170N, 172T, 178R, 190V, 191L, 200A, 223S, 226V, 243D, 268Y, 279A and 298I. In one embodiment, the H5 HA protein of the invention comprises amino acid residues 61D, 87I, 99A, 102A, 110N, 120S, 136S, 140D, 149S, 155N, 156T, 157P, 170N, 172T, 178R, 190V, 191L, 200A, 223N, 226V, 243D, 268Y, 279A and 298I. In one embodiment, the H5 HA protein of the invention comprises amino acid residues 61D, 87I, 99A, 102A, 110N, 120N, 136S, 140D, 149S, 155N, 156T, 157P, 170N, 172T, 178R, 190V, 191L, 200A, 223S, 226V, 243D, 268Y, 279A and 298I.

In one embodiment of the immunogenic composition of the invention, the H5 HA protein comprises the amino acid sequence as set forth in SEQ ID NO: 6. In one embodiment, the H5 HA protein of the invention comprises the amino acid sequence as set forth in SEQ ID NO: 5. In one embodiment, the H5 HA protein of the invention consists of the amino acid sequence as set forth in SEQ ID NO: 6. In one embodiment, the H5 HA protein of the invention consists of the amino acid sequence as set forth in SEQ ID NO: 5.

As used herein, the term "H5 HA protein of the invention" may be an isolated form of the H5 HA protein, or a non-isolated form of the H5 HA protein, for example the H5 HA protein contained in a cell culture. In one embodiment of the immunogenic composition of the invention, the H5

HA protein is a non-isolated form of the H5 HA protein. In one embodiment of the immunogenic composition of the invention, the H5 HA protein is an isolated form of the H5 HA protein.

In one embodiment of the immunogenic composition of the invention, the H5 HA protein is prepared by expressing a nucleic acid molecule encoding the H5 HA protein.

In one embodiment, the nucleic acid molecule of the invention may be further codon-optimized for expression in cells. The term "codon-optimized nucleic acid molecule" as used herein means a nucleic acid molecule that has been chosen such that the codons are optimal for expression in a particular system (such as a particular species or groups of species). Codon optimization does not alter the amino acid sequence of the coded protein. In one embodiment, the nucleic acid molecule of the invention is codon-optimized for expression in insect cells.

In one embodiment, the nucleic acid molecule of the invention comprises the nucleic acid sequence as set forth in SEQ ID NO: 10. In one embodiment, the nucleic acid molecule of the invention consists of the nucleic acid sequence as set forth in SEQ ID NO: 10. In one embodiment, the nucleic acid molecule of the invention comprises the nucleic acid sequence as set forth in SEQ ID NO: 11. In one embodiment, the nucleic acid molecule of the invention consists of the nucleic acid sequence as set forth in SEQ ID NO: 11.

The nucleic acid molecule of the invention can be comprised in an expression vector. In one embodiment, the expression vector of the invention is a virus, plasmid, cosmid, or phage. The vector may be composed of either DNA or RNA, preferably DNA.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Feigner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

In one embodiment, the expression vector of the invention is a viral vector.

In one embodiment, the expression vector of the invention is a herpes virus, such as Aujeszky's disease virus, equine herpes virus or herpes-simplex virus. In one embodiment, the expression vector of the invention is an adenovirus, such as porcine adenovirus. In one embodiment, the expression vector of the invention is a poxvirus, such as vaccinia virus, avipox virus, canarypox virus or swinepox virus.

In one embodiment, the viral vector is a recombinant baculovirus. In one embodiment, the recombinant baculovirus of the invention is derived from as BaculoGold (BD Biosciences Pharmingen, San Diego, Calif.). In one embodiment, the recombinant baculovirus of the invention is derived from Sapphire™ Baculovirus (Allele Biotechnology). In one embodiment, the recombinant baculovirus of the invention comprises the nucleic acid molecule encoding the H5 HA protein of the invention. In one embodiment, the recombinant baculovirus of the invention comprises the nucleic acid molecule as set forth in SEQ ID NO: 10. In one embodiment, the recombinant baculovirus of the invention comprises the nucleic acid molecule as set forth in SEQ ID NO: 11.

In one embodiment of the immunogenic composition of the invention, the H5 HA protein is contained in a cell culture. The cell culture of the invention may be the whole cell culture obtained from a cell culture process, including the cell and the culture medium, or a portion of the cell culture containing the HA protein, for example, the portion of the cell culture containing the HA protein that is obtained by filtration or any other separation step.

In one embodiment, the cell culture comprises the H5 HA protein, wherein the H5 HA protein comprises: (a) amino acid residues 120N or 120S, 155N, and 223N or 223S; and (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I; with numbering with reference to amino acid residues as set forth in SEQ ID NO:1. In one embodiment, the cell culture comprises the H5 HA protein, wherein the H5 HA protein comprises amino acid residues 61D, 87I, 99A, 102A, 110N, 120N, 136S, 140D, 149S, 155N, 156T, 157P, 170N, 172T, 178R, 190V, 191L, 200A, 223N, 226V, 243D, 268Y, 279A and 298I. In one embodiment, the cell culture comprises the H5 HA protein, wherein the H5 HA protein comprises amino acid sequence as set forth in SEQ ID NO: 6. In one embodiment, the cell culture comprises the H5 HA protein, wherein the H5 HA protein comprises an amino acid sequence as set forth in SEQ ID NO: 5.

The immunogenic composition of the invention further comprises an adjuvant. In one embodiment, the immunogenic composition is formulated in an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

In one embodiment, the immunogenic composition is formulated into a water-in-oil emulsion with a suitable adjuvant. The adjuvant can comprise oils and surfactants. In one embodiment, the adjuvant is MONTANIDE™ ISA 71R VG (Manufactured by Seppic Inc, Cat no: 365187). The adjuvant can be added in an amount of about 100 μg to about 10 mg per dose. Even more preferred the adjuvant is added in an amount of about 100 μg to about 10 mg per dose. Even more preferred the adjuvant is added in an amount of about 500 μg to about 5 mg per dose. Even more preferred the adjuvant is added in an amount of about 750 μg to about 2.5 mg per dose. Most preferred the adjuvant is added in an amount of about 1 mg per dose. In one embodiment, the immunogenic composition of the invention comprises about 7 parts of oil phase containing the adjuvant and about 3 parts of aqueous phase containing the H5 HA protein of the invention per dose.

It was surprisingly found that the immunogenic composition of the invention can result in a broader protection on poultry. The term "broader protection on poultry" as used herein encompasses a broad protection against different AIV H5 subtypes. Such subtypes encompass, or according to a further embodiment consist of H5N1, H5N2 and/or H5N6. According to a further embodiment, the term "broader protection on poultry" also encompasses the protection against different clades of AIV H5 subtypes. Such AIV H5 clades encompass or according to a further embodiment consist of 2.3.4.4, 2.3.2.1, 2.3.2.1d, 2.3.4.4d and/or 7.2.

In addition, the protection provided by the immunogenic composition of the invention has an early onset and a long-lasting period. The term "early onset period" or "early onset of protection" as used herein means that partial protection against infectious AIV H5 virus is obtainable 7 days after vaccination. Full protection against infectious AIV H5 virus is obtainable 14 days post vaccination. The term "long-lasting period" or "long-lasting protection on poultry" encompasses a protection period of at least 42 days post vaccination.

The immunogenic composition of the invention can provide protection on chicken with different days of age, even from newborns, i.e. day one of life. The immunogenic composition of the invention does not have to be limited to a certain route of administration, and the protection efficacy of the immunogenic composition of the invention is not affected by different routes of administration.

In another aspect, the invention also provides a method of preparing an immunogenic composition, comprising: (i) culturing cells containing an expression vector capable of expressing an H5 HA protein; and (ii) harvesting the H5 HA protein or the whole cell culture comprising the H5 HA protein, wherein the H5 HA protein comprises: (a) amino acid residues 120N or 120S, 155N, and 223N or 223S; and (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I; with numbering with reference to amino acid residues as set forth in SEQ ID NO:1.

In one embodiment of the method of the invention, the H5 HA protein comprises amino acid residues 61D, 87I, 99A, 102A, 110N, 120N, 136S, 140D, 149S, 155N, 156T, 157P, 170N, 172T, 178R, 190V, 191L, 200A, 223N, 226V, 243D, 268Y, 279A and 298I. In one embodiment, the H5 HA protein comprises an amino acid sequence as set forth in SEQ ID NO: 6. In one embodiment, the H5 HA protein comprises an amino acid sequence as set forth in SEQ ID NO: 5.

In one embodiment of the method of the invention, the expression vector is a recombinant baculovirus comprising the nucleic acid molecule of the invention. In one embodiment, the nucleic acid molecule of the invention is set forth in SEQ ID NO: 10. In one embodiment, the nucleic acid molecule of the invention is set forth in SEQ ID NO: 11. In one embodiment, the recombinant baculovirus is derived from a commercial product sold under the trademark Sapphire™ Baculovirus (Allele Biotechnology). In one embodiment, the cells are insect cells. In one embodiment, the insect cells are SF+ cells. In one embodiment, the SF+ cells are a commercial product sold by Protein Sciences Corporation (Meriden, Conn.).

In one embodiment of the method of the invention, the method comprises a step of preparing a recombinant baculovirus comprising the nucleic acid molecule of the invention. In one embodiment, the nucleic acid molecule of the invention is set forth in SEQ ID NO: 10. In one embodiment, the nucleic acid molecule of the invention is set forth in SEQ ID NO: 11. In one embodiment, the recombinant baculovirus is derived from a commercial product sold under the trademark Sapphire™ Baculovirus (Allele Biotechnology).

In one embodiment of the method of the invention, the method comprises a step of infecting cells with the recombinant baculovirus of the invention. In one embodiment, the cells are insect cells. In one embodiment, the insect cells are SF+ cells. In one embodiment, the SF+ cells are a commercial product sold by Protein Sciences Corporation (Meriden, Conn.).

In one embodiment of the method of the invention, the method comprises preparing a recombinant baculovirus comprising the nucleic acid molecule of the invention, and infecting insect cells with the recombinant baculovirus. In one embodiment, the recombinant baculovirus is derived from a commercial product sold under the trademark Sapphire™ Baculovirus (Allele Biotechnology). In one embodiment, the nucleic acid molecule of the invention is set forth in SEQ ID NO: 10. In one embodiment, the nucleic acid molecule of the invention is set forth in SEQ ID NO: 11. In one embodiment, the insect cells are SF+ cells. In one embodiment, the SF+ cells are a commercial product sold by Protein Sciences Corporation (Meriden, Conn.).

In one embodiment of the method of the invention, the method comprises: (i) preparing a recombinant baculovirus comprising the nucleic acid molecule of the invention; (ii) infecting insect cells with the recombinant baculovirus; (iii) culturing the insect cells in a culture medium; and (iv) harvesting the H5 HA protein of the invention or the whole cell culture comprising the H5 HA protein of the invention. In one embodiment, the recombinant baculovirus is derived from a commercial product sold under the trademark Sapphire™ Baculovirus (Allele Biotechnology). In one embodiment, the nucleic acid molecule of the invention is set forth in SEQ ID NO: 10. In one embodiment, the nucleic acid molecule of the invention is set forth in SEQ ID NO: 11. In one embodiment, the insect cells are SF+ cells. In one embodiment, the SF+ cells are a commercial product sold by Protein Sciences Corporation (Meriden, Conn.).

In one embodiment of the method of the invention, the culture medium for culturing the cells of the invention will be determined by those of skill in the art. In one embodiment, the culture medium is a serum-free insect cell medium. In one embodiment, the culture medium is Ex-CELL 420 (Ex-CELL® 420 serum-free medium for insect cells, Sigma-Aldrich, Cat. 14420C).

In one embodiment of the method of the invention, the insect cells are cultured under the condition suitable for the expression of the H5 HA protein. In one embodiment, the insect cells are incubated over a period of up to ten days, preferably from about two days to about ten days, more preferably from about four days to about nine days, and even more preferably from about five days to about eight days. In one embodiment, the condition suitable for culturing the insect cell comprises a temperature between about 22-32° C., preferably from about 24-30° C., more preferably from about 25-29° C., even more preferably from about 26-28° C., and most preferably about 27° C.

In one embodiment of the method of the invention, the method further comprises a step of inactivating the cell culture of the invention. Any conventional inactivation method can be used for purposes of the invention, including but not limited to chemical and/or physical treatments.

In one embodiment, the inactivation step comprises the addition of cyclized binary ethylenimine (BEI), preferably in a concentration of about 1 to about 20 mM, preferably of about 2 to about 10 mM, more preferably of about 5 mM or 10 mM. In one embodiment, the inactivation step comprises the addition of a solution of 2-bromoethyleneamine hydrobromide which will be cyclized to form BEI in NaOH.

In one embodiment, the inactivation step is performed between 25-40° C., preferably between 28-39° C., more preferably between 30-39° C., more preferably between 35-39° C. In one embodiment, inactivation step is performed for 24-72 h, preferably for 30-72 h, more preferably 48-72 h. In general, the inactivation step is performed until no replication of the viral vector is detectable.

In one embodiment of the method of the invention, the method further comprises a step of a neutralization step after the inactivation step. The neutralization step comprises adding of an equivalent amount of an agent that neutralizes the inactivation agent within the solution. In one embodiment, the inactivation agent is BEI. In one embodiment, the neutralization agent is sodium thiosulfate. In one embodiment, when the inactivation agent is BEI, an equivalent amount of sodium thiosulfate will be added. For example, in the event BEI is added to a final concentration of 5 mM, a 1.0M sodium thiosulfate solution is added to give a final minimum concentration of 5 mM to neutralize any residual BEI. In one embodiment, the neutralization step comprises adding of a sodium thiosulfate solution to a final concentration of 1 to 20 mM, preferably of 2 to 10 mM, more preferably of 5 mM or 10 mM, when the inactivation agent is BEI. In one embodiment, the neutralization agent is added after the inactivation step is completed, which means that no replication of the viral vector replication can be detected. In one embodiment, the neutralization agent is added after the inactivation step is performed for 24 h. In one embodiment, the neutralization agent is added after the inactivation step is performed for 30 h. In one embodiment, the neutralization agent is added after the inactivation step is performed for 48 h. In one embodiment, the neutralization agent is added after the inactivation step is performed for 72 h.

The amount of the H5 HA protein contained in the immunogenic composition of the invention can be quantitated by using any conventional methods known in the art, for example the Haemagglutination Assay (See *OIE Terrestrial Manual* 2015, Chapter 2.3.1 & 2.3.2, Avian Influenza (infection with avian influenza viruses)). In one embodiment, the amount of the H5 HA protein contained in the immunogenic composition of the invention is determined by haemagglutination test with chicken red blood cells, and the amount of the H5 HA protein can be expressed as hemagglutinin assay unit (HAU).

The term "HAU" refers to a unit of the activity for agglutinating red blood cells (RBC), and 1 HAU of hemagglutinin protein refers to the minimum unit that causes agglutination when the hemagglutinin is mixed with RBC. HAU can be assessed by a haemagglutination titer assay. In the assay, a sample containing a hemagglutinin protein is subjected to a two-fold serial dilution in a 96-well plate, and RBC solution is added to the wells. The value of HAU is the greatest dilution fold of the sample resulting in complete agglutination of the RBC. For example, if the greatest dilution fold of a 25 µl sample is 256, the amount of the hemagglutinin protein contained in the sample is 256 HAU per 25 µl.

To elicit an effective immune response according to the invention, the amount of the H5 HA protein contained in the immunogenic composition of the invention is at least 32 HAU per dose. Thus, the immunogenic composition of the invention comprises at least 32 HAU per dose of the H5 HA protein of the invention. In a further aspect, the immunogenic composition of the invention comprises at least 64 HAU per dose of the H5 HA protein of the invention. In a further aspect, the immunogenic composition of the invention comprises at least 128 HAU per dose of the H5 HA protein of the invention. In a further aspect, the immunogenic composition of the invention comprises at least 256 HAU per dose of the H5 HA protein of the invention.

The skilled person in the art can determine the upper limit of the amount of H5 HA protein just by routine testing. In general, the upper limit used by a skilled person will be in the range of about 1024 HAU per dose, but could also be higher. In a further aspect, the immunogenic composition of the invention comprises at least 32 to 1024 HAU per dose of the H5 HA protein of the invention. In a further aspect, the immunogenic composition of the invention comprises at least 64 to 1024 HAU per dose of the H5 HA protein of the invention. In a further aspect, the immunogenic composition of the invention comprises at least 128 to 1024 HAU per dose of the H5 HA protein of the invention. In a further aspect, the immunogenic composition of the invention comprises at least 256 to 1024 HAU per dose of the H5 HA protein of the invention.

Compared to the conventional whole virus inactivated vaccines that are required to be produced in Biosafety Level 2 or 3 (BSL-2, BSL-3), the above manufacture method for producing the H5 HA protein has been categorized to biosafety level 1 requirements.

In another aspect, the invention also provides a method for the prevention and/or treatment of infections caused by AIV, comprising administration of an effective amount of the immunogenic composition of the invention, to a subject in need thereof. The invention also provides the immunogenic composition of the invention for use in the prevention and/or treatment of infections caused by AIV.

As used herein, the term "prevention" refers to the reduction in the incidence of or severity of clinical signs of influenza infection up to an including the complete prevention of such clinical signs. The prevention protection efficacy of the immunogenic composition can be evaluated based on the survival rate of the vaccinated subject against different AIV clades. In one embodiment, the protection efficacy of the immunogenic composition is increased by at least 10%, more preferably at least 20%, still more preferably at least 30%, even more preferably at least 40%, more preferably at least 50%, still more preferably at least 60%, even more preferably at least 70%, more preferably at least 80%, still more preferably at least 90%, even more preferably at least 95%, and most preferably 100% in comparison to a subject that did not receive the vaccine of the invention but that were exposed to infectious levels of AIV. In one embodiment, the protection efficacy of the immunogenic composition is 100% on the vaccinated subject against different AIV clades.

In one embodiment, the subject in need thereof can be poultry, even more preferably bird, chicken, duck, turkey and the like. In one embodiment, the subject is chicken or duck.

In one embodiment, the AIV is H5 subtype. In one embodiment, the AIV is H5Nx. In one embodiment, the AIV is HPAI H5Nx circulating mainly in Asia, the Middle East and Africa. In one embodiment, H5Nx is H5N1, H5N2 and/or H5N6 In one embodiment, H5Nx is H5N1. In one embodiment, H5Nx is H5N2. In one embodiment, H5Nx is H5N6. In one embodiment, H5Nx is H5N1 and H5N2. In one embodiment, H5Nx is H5N2 and H5N6. In one embodiment, the AIV is clade 2, preferably clade 2.3, and more preferably clades 2.3.4 and 2.3.2. In one embodiment, the AIV is clade 2.3.4.4, 2.3.2.1, 2.3.2.1d, or 2.3.4.4d. In one embodiment, the AIV is clade 7.2.

H5Nx of subtype H5N1, H5N2 and/or H5N6 are well known in the art.

As used herein, the term "clade" refers to a group of biological taxa (such as species) that includes all descendants of one common ancestor. A/goose/Guangdong/1/96 was considered the progenitor for all H5 lineage viruses and was designated as clade 0. This nomenclature is now used to distinguish variant groups of H5 HA gene, so far about 20 distinct clades of the virus has been formally identified. Other than clade 0, additional 9 clades (1-9) were described and defined based on all the sequences deposited. However, most of the clades of viruses became extinct over the time. The H5 lineage virus has continued to circulate in poultry and wild birds in parts of Asia, the Middle East, and Africa and continued to evolve. The most dominant clade resulted in endemic infections in several different countries is clade 2 viruses, and further sublineages resulted from antigenic drift have been described as 2nd, 3rd, 4th and even 5th order clade. The nomenclature and the emerged clade can be seen from WHO/OIE/FAO. Continuing progress towards a unified nomenclature for the highly pathogenic H5N1 avian influenza viruses: divergence of clade 2.2 viruses. Influenza Other Respiration Viruses. *Letter.* 2009; 3:59-62; WHO/OIE/FAO. Continued evolution of highly pathogenic avian influenza A (H5N1): updated nomenclature. *Influenza Other Respiration Viruses* 2012; 6:1-5; and WHO-OIE-FAO HNEWG. Revised and updated nomenclature for highly pathogenic avian influenza A (H5N1) viruses. *Influenza Other Respiration Viruses* 2014; 8:384-388.

For instance H5Nx of clade 2.3.4.4 are described in Lee et al., *Emerging Infectious Diseases,* 2016; Volume 22(7) pp. 1283-1284 and in Lee et al., *Journal Veterinary Science*

2017; Vol. (S1), pp. 269-280. Avian influenza isolate A/common magpie/Hong Kong/5052/2007 (H5N1) described in Smith et al., *Emerging Infectious Diseases,* 2009; Volume 15(3), pp. 402-407 belongs to clade 2.3.2.1. Further H5Nx isolates of clade 2.3.2.1, including A/chicken/India/ CL03485/2011 (H5N1) or A/chicken/India/CA0302/2011 (H5N1) are described, for instance in Bhat et al., 2015, *Microbial Pathogenesis*; volume 88, pp. 87-93. Further H5Nx of subclades of 2.3.2.1 as well as of 2.3.4.4, including 2.3.4.4d such as for example A/duckNietnam/HU1-1507/2014 (H5N6) or A/duck/Vietnam/HU1-1151/2014 (H5N6) are described in *Nguyen et al.,* 2019, *Scientific Reports* 9; Article 7723, pp. 1-13. H5Nx isolates of clade 7.2, including for example (A/chicken/Gansu/62012 (H5N1)) are described and characterized for example in Liu et al., *Journal of Virology* 2016, Volume 90(21), pp. 9797-9804.

In one embodiment, the immunogenic composition of the invention can be administrated via subcutaneous (S.C.) or intramuscular (I.M.) administration.

The times of administration of the immunogenic composition of the invention can be determined by a person skilled in the art according to practical requirements. For example, as for white broilers whose life span is about 40-50 days, the immunogenic composition of the invention can be administrated in a single dose; as for yellow broilers whose life span is about 70 days, the immunogenic composition of the invention can be administrated in two doses; and as for the chicken such as breeders whose life span is more than one year or longer, the immunogenic composition of the invention can be administrated in multiple doses. In one embodiment, the immunogenic composition of the invention is administrated in a single dose administration. In one embodiment, the immunogenic composition of the invention is administrated in multiple doses administration, such as 2, 3, 4, 5, 6, 7, 8, 9, or 10 doses. In one embodiment, the interval between two doses is about 4-6 weeks, such as 4 weeks, 5 weeks or 6 weeks.

A person skilled in the art can also determine when the first dose of administration is given according to practical requirements. For example, when chicken are vaccinated. In one embodiment, the immunogenic composition of the invention can be firstly administrated at day 1 of age or later, at day 7 of age or later, at day 10 of age or later, at day 15 of age or later, or at day 21 of age or later. In one embodiment, the immunogenic composition of the invention is administrated at day 1 of age or later, at day 7 of age or later, at day 10 of age or later, at day 15 of age or later, or at day 21 of age or later. In one embodiment, the immunogenic composition of the invention is administrated from day 1 of age, from day 7 of age, from day 10 of age, from day 15 of age, or from day 21 of age in a single-administration. In one embodiment, the immunogenic composition of the invention is administrated from day 1 of age in a single-administration.

In another aspect, the invention also provides a method of differentiating animals naturally infected with AIV from animals vaccinated with the vaccine or the immunogenic composition of the invention. The invention also provides use of the immunogenic composition of the invention in preparation of an agent for differentiating between animals naturally infected with AIV and the vaccinated animals.

In one embodiment, the method comprises: a) analyzing a sample of an animal in an immuno test and/or genomic analytical test for the presence of an avian influenza marker which is not present in the immunogenic composition but present in the naturally infected animal, wherein the immuno test is an enzyme immunoassay or enzyme linked immunosorbent assay, or an agar gel precipitation assay, or a western blot assay b) determining whether the sample is positive or negative for the avian influenza marker, and c) correlating the test results with the status of the tested animal, wherein an animal that is positive for the avian influenza marker is a naturally infected animal and the animal that is negative for the avian influenza marker is an animal that is vaccinated with the immunogenic composition or the vaccine of the invention.

In one embodiment, the method comprises: a) analyzing a sample of an animal in an immuno test and/or genomic analytical test for the presence of an avian influenza marker which is specific for the immunogenic composition but not present in the naturally infected animal, wherein the immuno test is an enzyme immunoassay or enzyme linked immunosorbent assay, b) determining whether the sample is positive or negative for the avian influenza marker, and c) correlating the test results with the status of the tested animal, wherein an animal that is positive for the avian influenza marker is an animal that is vaccinated with the immunogenic composition or the vaccine of the invention.

In one embodiment, the animal can be poultry, even more preferably bird, chicken, duck, turkey and the like. In one embodiment, the animal is chicken or duck.

In one embodiment, the AIV is H5 subtype. In one embodiment, the AIV is H5Nx. In one embodiment, the AIV is HPAI H5Nx circulating mainly in Asia, the Middle East and Africa. In one embodiment, H5Nx is H5N1, H5N2 and/or H5N6. In one embodiment, H5Nx is H5N1. In one embodiment, H5Nx is H5N2. In one embodiment, H5Nx is H5N6. In one embodiment, H5Nx is H5N1 and H5N2. In one embodiment, H5Nx is H5N2 and H5N6.

In one embodiment, the AIV is clade 2, preferably clade 2.3, and more preferably clades 2.3.4 and 2.3.2. In one embodiment, the AIV is clade 2.3.4.4 or 2.3.2.1, 2.3.2.1d, or 2.3.4.4d. In one embodiment, the AIV is clade 7.2.

Animals vaccinated with the vaccine or the immunogenic composition comprising the H5 HA protein of the invention will only have antibody response against this specific antigen, while negative response to other viral components. A further advantage of the invention is that it benefits a DIVA concept with specific ELISA for differentiating between AIV infected animals and vaccinated animals.

In another aspect, the invention also provides kits, comprising the H5 HA protein of the invention, the nucleic acid molecule, the vector, the cell, or the vaccine or the immunogenic composition of the invention. In one embodiment, the kits can be used for the subject such as poultry, even more preferably bird, chicken, duck, turkey and the like. In one embodiment, when chicken are vaccinated, the H5 HA protein, the vaccine or the immunogenic composition of the invention can be used for vaccination at day 1 of age or later, at day 7 of age or later, at day 10 of age or later, at day 15 of age or later, or at day 21 of age or later. In one embodiment, the immunogenic composition of the invention is administrated from day 1 of age, from day 7 of age, from day 10 of age, from day 15 of age, or from day 21 of age in a single-administration. In one embodiment, the immunogenic composition of the invention is administrated from day 1 of age in a single-administration.

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall comprise pluralities and plural terms shall comprise the singular. Herein, the use of "or" means "and/or" unless stated otherwise. Furthermore, the use of the term "including", as well as other forms such as "comprises" and "comprised" is not limiting. All patents and publications referred to herein are incorporated by reference herein.

The practice of the invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is also to be understood that the terminology used herein is for the purpose of describing particular embodiments of the invention only, and is not intended to be limiting. It must be noted that, as used in this specification and the appended claims, the singular forms "a", "an" and "the" comprise plural referents unless the content clearly dictates otherwise. Thus, for example, reference to "an antigen" comprises a mixture of two or more antigens, reference to "an carrier" comprises mixtures of two or more carriers, and the like.

Clauses

The following clauses are also described herein and part of disclosure of the invention:

1. An immunogenic composition comprising a hemagglutinin protein of avian influenza virus H5 subtype, wherein the hemagglutinin protein comprises:
   (a) amino acid residues 120N or 120S, 155N, and 223N or 223S; and
   (b) one or more amino acid residues selected from the group consisting of: 61D, 87I, 99A, 102A, 110N, 136S, 140D, 149S, 156T, 157P, 170N, 172T, 178R, 190V, 191L, 200A, 226V, 243D, 268Y, 279A and 298I;
with numbering with reference to amino acid residues as set forth in SEQ ID NO:1

2. The immunogenic composition of clause 1, wherein the hemagglutinin protein comprises:
   (a) amino acid residues 61D, 87I, 99A, 102A, 110N, 120N, 136S, 140D, 149S, 155N, 156T, 157P, 170N, 172T, 178R, 190V, 191L, 200A, 223N, 226V, 243D, 268Y, 279A and 298I;
   (b) an amino acid sequence as set forth in SEQ ID NO: 6; or
   (c) an amino acid sequence as set forth in SEQ ID NO: 5.

3. The immunogenic composition of clauses 1 or 2, wherein the hemagglutinin protein comprises an amino acid sequence as set forth in SEQ ID NO: 6.

4. The immunogenic composition of clauses 1 or 2, wherein the hemagglutinin protein comprises an amino acid sequence as set forth in SEQ ID NO: 5.

5. The immunogenic composition of any one of clauses 1-4, wherein the hemagglutinin protein is contained in a cell culture, and the cell culture is prepared by culturing cells containing an expression vector capable of expressing the hemagglutinin protein as defined in any one of clauses 1-4.

6. The immunogenic composition of any one of clauses 1-5, wherein the expression vector comprises a nucleic acid molecule encoding the hemagglutinin protein as defined in any one of clauses 1-4.

7. The immunogenic composition of clause 6, wherein the nucleic acid molecule is set forth in SEQ ID NO: 10.

8. The immunogenic composition of clause 6, wherein the nucleic acid molecule is set forth in SEQ ID NO: 11.

9. The immunogenic composition of any one of clauses 5-8, wherein the expression vector is a baculovirus, and the cells are insect cells.

10. The immunogenic composition of clauses 5-9, wherein the cell culture is subjected to an inactivation step, preferably an inactivation step by binary ethyleneimine.

11. The immunogenic composition of any one of clauses 5-10, wherein the immunogenic composition comprises a portion or all of the cell culture.

12. The immunogenic composition of any one of clauses 1-11, wherein the immunogenic composition further comprises an adjuvant.

13. The immunogenic composition of clause 12, wherein the adjuvant is a water-in-oil emulsion.

14. The immunogenic composition of any one of clauses 1-13, wherein the immunogenic composition is administered in a single-dose administration or multiple doses administration; and/or
the immunogenic composition is administered subcutaneously or intramuscularly; and/or
the immunogenic composition is to be administered to an animal at 1 day of age or older, at 7 day of age or older, at 10 day of age or older, at 15 day of age or older, or at 21 day of age or older.

15. The immunogenic composition of any one of clauses 1-14, wherein the immunogenic composition is to be administered to an animal at 1 day of age or older, at 7 day of age or older, at 10 day of age or older, at 15 day of age or older, or at 21 day of age or older.

16. The immunogenic composition of any one of clauses 1-14, wherein the immunogenic composition is to be administered to an animal from day 21 of age.

17. The immunogenic composition of any one of clauses 1-14, wherein the immunogenic composition is to be administered to an animal from day 15 of age.

18. The immunogenic composition of any one of clauses 1-14, wherein the immunogenic composition is to be administered to an animal from day 7 of age.

19. The immunogenic composition of any one of clauses 1-14, wherein the immunogenic composition is to be administered to an animal from day 1 of age.

20. The immunogenic composition of any one of clauses 1-14, wherein the immunogenic composition is to be administered to an animal from day 1 of age.

21. The immunogenic composition of any one of clauses 1-20, for use in the prevention and/or treatment of infections caused by an avian influenza virus, preferably by H5Nx, more preferably by one or more of H5N1, H5N2 and H5N6.

22. The immunogenic composition of any one of clauses 1-20, for use in the prevention and/or treatment of infections caused by an H5N1 avian influenza virus.

23. The immunogenic composition of any one of clauses 1-20, for use in the prevention and/or treatment of infections caused by an H5N2 avian influenza virus.

24. The immunogenic composition of any one of clauses 1-20, for use in the prevention and/or treatment of infections caused by an H5N6 avian influenza virus.

25. The immunogenic composition of any one of clauses 1-20, for use in the prevention and/or treatment of infections caused by an H5Nx avian influenza virus of clade 2, preferably clade 2.3, and more preferably clades 2.3.4 or 2.3.2.

26. The immunogenic composition of any one of clauses 1-20, for use in the prevention and/or treatment of infections caused by an H5Nx avian influenza virus of clade 2.

27. The immunogenic composition of any one of clauses 1-20, for use in the prevention and/or treatment of infections caused by an H5Nx avian influenza virus of clade 2.3.

28. The immunogenic composition of any one of clauses 1-20, for use in the prevention and/or treatment of infections caused by an H5Nx avian influenza virus of clade 2.3.4.

29. The immunogenic composition of any one of clauses 1-20, for use in the prevention and/or treatment of infections caused by an H5Nx avian influenza virus of clade 2.3.4.4.

30. The immunogenic composition of any one of clauses 1-20, for use in the prevention and/or treatment of infections caused by an H5Nx avian influenza virus of clade 2.3.4.4d.

31. The immunogenic composition of any one of clauses 1-20, for use in the prevention and/or treatment of infections caused by an H5Nx avian influenza virus of clade 2.3.2.

32. The immunogenic composition of any one of clauses 1-20, for use in the prevention and/or treatment of infections caused by an H5Nx avian influenza virus of clade 2.3.2.1

33. The immunogenic composition of any one of clauses 1-20, for use in the prevention and/or treatment of infections caused by an H5Nx avian influenza virus of clade 2.3.2.1d.

34. The immunogenic composition of any one of clauses 1-20, for use in the prevention and/or treatment of infections caused by an H5Nx avian influenza virus of clade 7.2.

35. The immunogenic composition of any one of clauses 1-34, wherein the immunogenic composition is administered in a single-dose administration.

36. The immunogenic composition of any one of clauses 1-34, wherein the immunogenic composition is administered as single-dose administration and wherein said single-dose is effective in the prevention and/or treatment of infections caused by an avian influenza virus.

37. The immunogenic composition of any one of clauses 1-34, wherein the immunogenic composition is administered as single-dose administration and wherein said single-dose is effective in the prevention and/or treatment of infections caused by one or more of H5N1, H5N2 and H5N6.

38. The immunogenic composition of any one of clauses 1-34, wherein the immunogenic composition is administered as single-dose administration and wherein said single-dose is effective in the prevention and/or treatment of infections caused by any H5Nx as cited in clauses 22-34.

39. A method of differentiating animals naturally infected with an avian influenza virus from animals vaccinated with the immunogenic composition of any one of clauses 1-13, comprising
(a) analyzing a sample of an animal in an immuno test and/or genomic analytical test for the presence of an avian influenza marker which is not present in the immunogenic composition but present in the naturally infected animal, wherein the immuno test is an enzyme immunoassay or enzyme linked immunosorbent assay,
(b) determining whether the sample is positive or negative for the avian influenza marker, and
(c) correlating the test results with the status of the tested animal, wherein an animal that is positive for the avian influenza marker is a naturally infected animal and the animal that is negative for the avian influenza marker is an animal that is vaccinated with the immunogenic composition of any one of clauses 1-13.

40. A method of differentiating animals naturally infected with an avian influenza virus from animals vaccinated with the immunogenic composition of any one of clauses 1-13, comprising
(a) analyzing a sample of an animal in an immuno test and/or genomic analytical test for the presence of an avian influenza marker which is specific for the immunogenic composition but not present in the naturally infected animal, wherein the immuno test is an enzyme immunoassay or enzyme linked immunosorbent assay,
(b) determining whether the sample is positive or negative for the avian influenza marker, and
(c) correlating the test results with the status of the tested animal, wherein an animal that is positive for the avian influenza marker is an animal that is vaccinated with the immunogenic composition of any one of clauses 1-13.

Sequences Overview

The following sequences are detailed and disclosed hereby in the present invention:

SEQ ID NO: 1: The amino acid sequence of the HA protein of strain duck/China/E319-2/03 but lacking the signal peptide of the amino terminus.

SEQ ID NO: 2: The amino acid sequence of H5Con1.

SEQ ID NO: 3: The amino acid sequence of H5Con3.

SEQ ID NO: 4: The amino acid sequence of H5Con5.

SEQ ID NO: 5: The amino acid sequence of H5Con5Mut.

SEQ ID NO: 6: The amino acid sequence from position 60 to 300 of H5Con5Mut.

SEQ ID NO: 7: Optimized nucleic acid sequences of H5Con1.

SEQ ID NO: 8: Optimized nucleic acid sequences of H5Con3.

SEQ ID NO: 9: Optimized nucleic acid sequences of H5Con5.

SEQ ID NO: 10: Optimized nucleic acid sequence of H5ConMut.

SEQ ID NO: 11: Optimized nucleic acid sequence encoding the amino acid sequence from position 60 to 300 of H5Con5Mut.

BRIEF DESCRIPTION OF THE DRAWINGS

The following drawings form part of the invention and are comprised to further demonstrate certain aspects of the invention. The invention may be better understood by reference to one or more of these drawings in combination with the detailed description of specific embodiments presented herein.

FIG. 1: H5Con1 sequence was generated with sequential method from 444 sequences isolated from year 1996 to 2012.

FIG. 2: H5Con3 sequence was generated with one round method from 297 sequences of specific clades isolated from year 1996 to 2012.

FIG. 3: H5Con5 sequence was generated with one round method from 196 sequences isolated from year 2005 to 2012.

FIG. 4: Construction of the transfer plasmid pVL1393-H5Con5Mut.

EXAMPLES

The following examples are included to further illustrate the invention described herein and to demonstrate embodiments of the invention. It should be appreciated by those of skill in the art that the techniques disclosed in the examples which follow represent techniques discovered by the inventors to function well in the practice of the invention, and thus can be considered to constitute modes for its practice. However, those of skill in the art should, in light of the present disclosure, appreciate that many changes can be made in the specific embodiments which are disclosed and still obtain a like or similar result which are within the spirit and scope of the invention.

Example 1: Generation of the H5 HA Consensus Amino Acid Sequences and the Mutant Thereof Generation of H5N1 Influenza HA Consensus Amino Acid Sequence 1

To generate H5N1 influenza HA consensus amino acid sequence 1 (H5Con1), 444 Avian H5N1 influenza HA amino acid sequences isolated in China from year 1996 to year 2012 were collected and analyzed. The 444 HA amino acid sequences are composed of clades 0, clade 2.2, clade 2.3.2, clade 2.3.2.1, clade 2.3.4, clade 2.4, clade 2.5, clade 3, clade 4, clade 5, clade 6 clade 7 and clade 9. FIG. 1 shows a sequential method of generating H5Con1 from 444 amino acid sequences isolated from year 1996 to 2012. First, 13 tier 1 consensus amino acid sequences were generated, and each tier represents an individual clade using (1) 36 of clade 0 sequences; (2) 31 of clade 2.2 sequences; (3) 8 of clade 2.3.2; (4) 49 of clade 2.3.2.1, (5) 2 of clade 2.3.3; (6) 210 of clade 2.3.4; (7) 18 of clade 2.4; (8) 6 of clade 2.5; (9) 9 of clade 3; (10) 5 of clade 4; (11) 8 of clade 5; (12) 3 of clade 6; (13) 34 of clade 7; and (14) 21 of clade 9. The final consensus amino acid sequence is the tier 2 consensus amino acid sequence which was generated by aligning and analyzing all 13 tier 1 consensus amino acid sequences with MEGA 5.0 software. This final consensus amino acid sequence was designated as H5Con1 (SEQ ID NO: 2).

Generation of H5N1 Influenza HA Consensus Sequence 3

To generate H5N1 influenza HA consensus amino acid sequence 3 (H5Con3), 297 Avian H5N1 influenza HA amino acid sequences isolated in China from year 1996 to year 2012 were collected and analyzed. The 297 HA amino acid sequences are composed of specific clades only, i.e. clade 2.3.2.1, clade 2.3.4, and clade 7. FIG. 2 shows one round method of generating H5Con3 from 297 amino acid sequences of specific clades isolated from year 1996 to 2012. The final consensus amino acid sequence was generated by aligning and analyzing (1) 49 of clade 2.3.2.1, (2) 214 of clade 2.3.4; and (3) 34 of clade 7 with MEGA 5.0 software. This final consensus amino acid sequence was designated as H5Con3 (SEQ ID NO: 3).

Generation of H5N1 Influenza HA Consensus Amino Acid Sequence 5

To generate H5N1 influenza HA consensus amino acid sequence 5 (H5Con5), 196 Avian H5N1 influenza HA amino acid sequences isolated in China from year 2005 to year 2012 were collected and analyzed. The 196 HA amino acid sequences are from clades 0, 2.2, 2.3.1, 2.3.2, 2.3.2.1, 2.3.4, 2.4, 7 and 9. FIG. 3 shows one round method of generating H5Con5 from 196 amino acid sequences isolated from year 2005 to 2012. Total of 196 amino acid sequences were aligned simultaneously with MEGA 5.0 software. The final consensus amino acid sequence was designated as H5Con5 (SEQ ID NO: 4).

The strategies of generating H5Con1, H5Con3 and H5Con5 are summarized in Table 1.

TABLE 1

Summary table of three consensus amino acid sequences

| | Sequence pool | Alignment Strategy |
|---|---|---|
| H5Con1 | All amino acid sequences (444 in total) | Sequential |
| H5Con3 | Clades 2.3.4 + 2.3.2.1 + 7.0 only | One round |
| H5Con5 | 196 amino acid sequences: 2005-2012 | One round |

Generation of H5N1 Influenza HA Consensus Amino Acid Sequence 5 Mutant

To generate H5N1 influenza HA consensus amino acid sequence 5 mutant (H5Con5Mut), two amino acid mutations were introduced to the amino acid sequence of H5Con5. At amino acid positions 120 and 223, both of the Serines (S) were mutated to Asparagines (N), i.e. S120N, and S223N. The amino acid sequence of H5Con5Mut was shown by SEQ ID NO: 5.

Analysis of H5Con1, H5Con3 and H5Con5

Table 2 shows the identity percentage of the consensus amino acid sequences of H5Con1, H5Con3 and H5Con5 and sequences from prevalent clades. Table 3 further shows the amino acid usage of each of the consensus amino acid sequences of H5Con1, H5Con3 and H5Con5 at some predicted antigenic sites of H5 HA protein.

TABLE 2

Summary of identity percentage of the consensus amino acid sequences of H5Con1, H5Con3 and H5Con5 and sequences from prevalent clades

| | Identity percentage | | | | | | | | |
|---|---|---|---|---|---|---|---|---|---|
| Clade | 2.3.2.1 | 2.3.4 | 2.2 | 2.3.1 | 2.3.2 | 2.4 | 7 | 0 | 9 |
| H5Con1 | 94.89 | 98.06 | 98.42 | 99.47 | 98.94 | 99.30 | 96.83 | 98.06 | 98.77 |
| H5Con3 | 95.25 | 98.94 | 97.54 | 98.94 | 98.77 | 98.24 | 96.48 | 97.01 | 97.71 |
| H5Con5 | 94.72 | 99.24 | 97.54 | 98.94 | 98.77 | 98.24 | 96.48 | 97.01 | 97.71 |

TABLE 3

Summary of amino acid usage of each of the consensus amino acid sequences of H5Con1, H5Con3 and H5Con5 at the predicted antigenic sites of H5 HA protein.

| | 61 | 87 | 99 | 102 | 110 | 136 | 140 | 149 | 156 | 157 | 170 |
|---|---|---|---|---|---|---|---|---|---|---|---|
| 2.3.2.1 | N | I | A | A | N | D | D | A | N | S | D |
| 2.3.4 | D | I | A | A | N | S | D | S | T | P | N |
| 7 | D | I | A | A | D | S | N | S | K | P | N |

TABLE 3-continued

Summary of amino acid usage of each of the consensus amino acid sequences of H5Con1, H5Con3 and H5Con5 at the predicted antigenic sites of H5 HA protein.

|         | 61 | 87 | 99 | 102 | 110 | 136 | 140 | 149 | 156 | 157 | 170 |
|---------|----|----|----|-----|-----|-----|-----|-----|-----|-----|-----|
| 2.3.2.1 | N  | I  | A  | A   | N   | D   | D   | A   | N   | S   | D   |
| 2.3.4   | D  | I  | A  | A   | N   | S   | D   | S   | T   | P   | N   |
| H5Con1  | D  | I  | A  | A   | N   | S   | D   | S   | K   | S   | N   |
| H5Con3  | D  | I  | A  | A   | N   | S   | D   | S   | N   | P   | N   |
| H5Con5  | D  | I  | A  | A   | N   | S   | D   | S   | T   | P   | N   |

|         | 172 | 178 | 190 | 191 | 200 | 226 | 243 | 268 | 279 | 298 |
|---------|-----|-----|-----|-----|-----|-----|-----|-----|-----|-----|
| 2.3.2.1 | A   | K   | V   | L   | E   | V   | D   | Y   | T   | I   |
| 2.3.4   | T   | R   | I   | L   | A   | V   | D   | Y   | A   | I   |
| 7       | T   | R   | V   | L   | A   | V   | E   | Y   | A   | M   |
| H5Con1  | A   | R   | V   | L   | A   | V   | D   | Y   | A   | M   |
| H5Con3  | T   | R   | V   | L   | E   | V   | D   | Y   | A   | I   |
| H5Con5  | T   | R   | V   | L   | A   | V   | D   | Y   | A   | I   |

It can be seen from Table 2 and 3 that H5Con1, H5Con3 and H5Con5 are different in amino acid sequences compared with the sequences from each of the prevalent clades, and also have some amino acid changes in the antigenic sites among three different prevalent clades.

Example 2: Optimization of the Nucleic Acid Sequences of H5Con1, H5Con3, H5Con5 and H5Con5Mut, the Construction of Recombinant Baculovirus Expression Systems and the Expression of H5Con1, H5Con3, H5Con5 and H5Con5Mut in Insect Cells Optimization of the Nucleic Acid Sequences of H5Con1, H5Con3, H5Con5 and H5Con5Mut To optimize for better expression, each of amino acid sequence of H5Con1, H5Con3 and H5Con5 as identified in Example 1 was reversely deduced into the corresponding nucleic acid sequence by Vector NTI software and optimized for expression in insect cells of Baculovirus Expression System (Allele Biotechnology, CAT ABP-BVP-10002). The optimized nucleic acid sequences of H5Con1, H5Con3 and H5Con5 were synthesized by GenScript (GenScript, NJ, USA). The optimized nucleic acid sequences of H5Con1, H5Con3 and H5Con5 were shown by SEQ ID NOs: 7-9 respectively. The optimized nucleic acid sequence of H5Con5Mut was generated by using a kit for site-directed mutagenesis (QuickChange Site-directed Mutagenesis kit, Cat #200518, Agilent) based on the optimized nucleic acid sequence of H5Con5. The optimized nucleic acid sequence of H5ConMut was shown by SEQ ID NO: 10.

Figure 4:
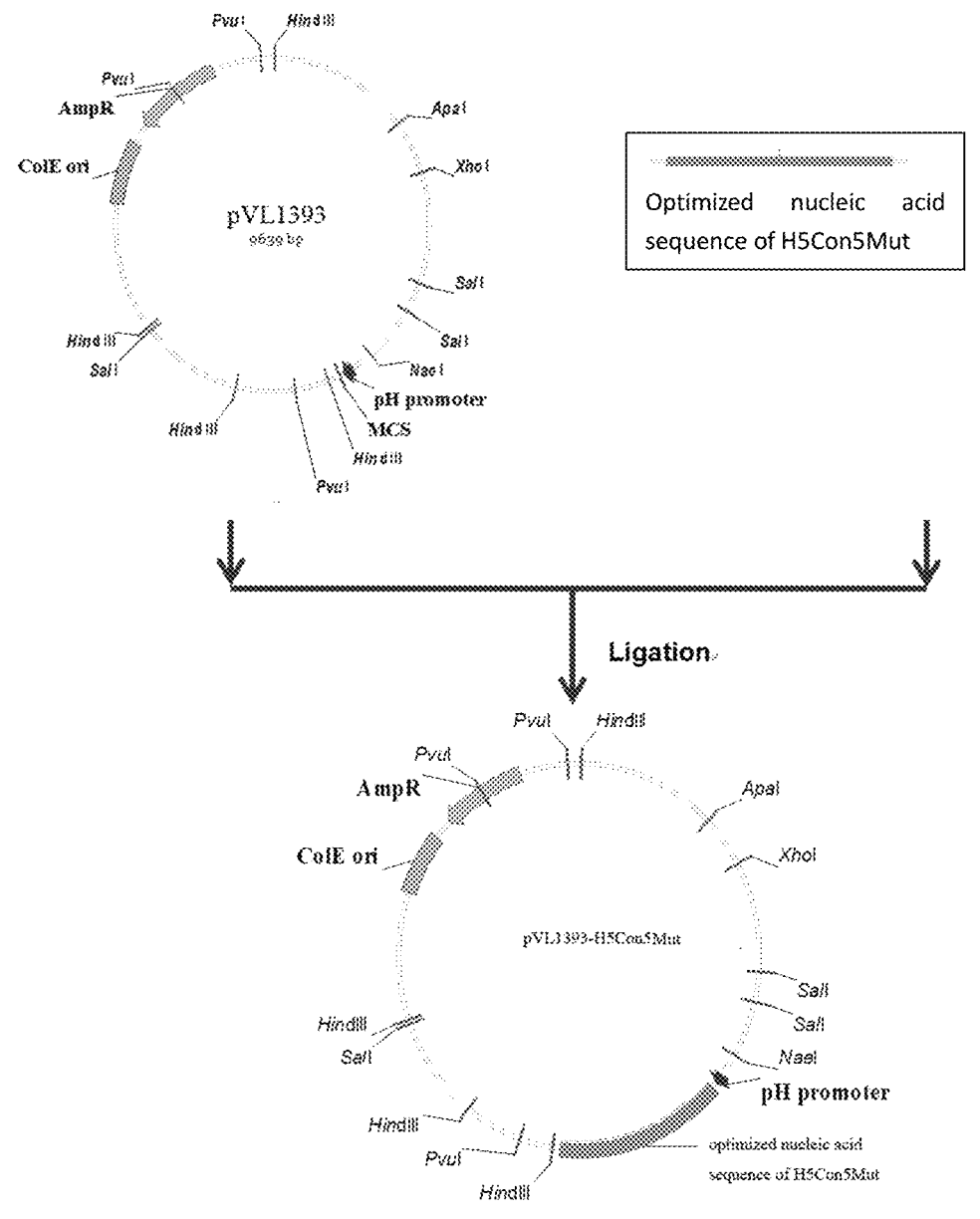

Construction of Recombinant Baculovirus Expression Systems, and the Expression of H5Con1, H5Con3, H5Con5 and H5Con5Mut in Insect Cells Each of the optimized nucleic acid sequences of H5Con1, H5Con3, H5Con5 and H5Con5Mut as prepared above was inserted into the Baculovirus expression system transfer vector pVL1393 which was included in the Sapphire™ Baculovirus DNA and Transfection Kit (Allele Biotechnology, CAT ABP-BVD-10002), so as to generate the transfer plasmids, designated as pVL1393-H5Con1, pVL1393-H5Con3, pVL1393-H5Con5, and pVL1393-H5Con5Mut, respectively. FIG. 4 exemplarily shows the construction of the transfer plasmid pVL1393-H5Con5Mut.

Each of pVL1393-H5Con1, pVL1393-H5Con3, pVL1393-H5Con5, and pVL1393-H5Con5Mut was then co-transfected with linearized wild type Sapphire™ Baculovirus DNA (Sapphire™ Baculovirus DNA and Transfection Kit; Allele Biotechnology, CAT ABP-BVD-10002) into the sf9 insect cells (Invitrogen, Cat #B825-01, Lot #1030672), so as to obtain rescued recombinant baculoviruses. The recombinant baculoviruses containing the optimized nucleic acid sequences of H5Con1, H5Con3, H5Con5 and H5Con5Mut were designated as rBacH5Con1, rBacH5Con3, rBacH5Con5 and rBacH5Con5Mut, respectively. And the transfected sf9 cells containing each of recombinant baculoviruses were obtained.

The transfected sf9 cells as prepared above were cultured at 27° C. incubator for four days, and the supernatant of the cell culture was harvested. To get pure recombinant virus, the harvested supernatant was then subjected to plaque purification. Three rounds of plaque purifications were conducted, and the virus plaques containing rBacH5Con1, rBacH5Con3, rBacH5Con5 and rBacH5Con5Mut respectively were picked up after the third round of plaque purification, so as to obtain purified rBacH5Con1, rBacH5Con3, rBacH5Con5 and rBacH5Con5Mut.

Each of the above purified rBacH5Con1, rBacH5Con3, rBacH5Con5 and rBacH5Con5Mut was further propagated in a suspension cultured insect cell line SF+ cells (Ex-CELL® 420 serum-free medium for insect cells, Sigma-Aldrich, Cat. 14420C) in shaking flasks. In brief, the SF+ cells (Protein Sciences Corporation, Meriden, CT) was seeded into a shaking flask at the density of $10^6$ cells/ml, and each of the above purified rBacH5Con1, rBacH5Con3, rBacH5Con5 and rBacH5Con5Mut was inoculated into SF+ cells (Protein Sciences, Inc., Meriden, CT) with MOI=0.01 to MOI=1. The inoculated SF+ cells were cultured at EX-CELL 420 medium at 27° C., with the shaking speed of 80-120 rpm/min for 3-7 days, and the cell culture suspensions containing the expressed H5Con1, H5Con3, H5Con5 and H5Con5Mut respectively were harvested later for the next step. The harvested cell culture suspensions comprised a cell count between 0.5-1.5×$10^6$ cells/ml.

Example 3: Determination of HAU of the Cell Culture Suspensions

The HAU of the cell culture suspensions containing H5Con1, H5Con3, H5Con5 and H5Con5Mut respectively was tested by Haemagglutination Assay (See OIE Terrestrial Manual 2015, Chapter 2.3.1 & 2.3.2, Avian Influenza (infection with avian influenza viruses)) with a two-fold serial dilution method. In brief, 10 ml of RBC (from Southern Regent Plant, Zhejiang Province) was centrifuged at 500 g for 20 min, and 1 volume of 4% centrifuged RBC was added into 3 volume of PBS to prepare 1% RBC. 25 µl of PBS was dispensed into well 1 to well 11 in 96-well plate. 25 ul of each of the cell culture suspensions was added into well 1 to well 11, and then was subjected to a serial dilution serial dilution from 1:2 to 1:2048 fold. 25 µl of 1% RBC was added to all wells and was incubated at room temperature for about 40 min.

The negative wells appeared as dots in the center of the wells, and positive results formed a uniform reddish color across the well. The endpoint of the dilution corresponds to the greatest dilution of the sample resulting in complete agglutination of the RBC. The results showed that the HAU of the cell culture suspensions of H5Con1, H5Con3, H5Con5 and H5Con5Mut was greater than 71.1 HAU/25 µl (corresponding to 256 HAU/90 ul or 256 HAU/dose).

Example 4: Preparation of Immunogenic Compositions

The harvested cell culture suspensions with HAU greater than 256/dose were further subjected to a binary ethyleneimine (BEI)-treatment by adding 10 mM BEI solution at 37° C. for 72 hours, so as to inactivate the infectivity of Baculovirus. Then 10 mM 4° C. sodium thiosulfate solution was added to neutralize BEI residue.

After the inactivation, the HAU of the cell culture suspensions was assessed again, and the inactivated cell culture suspensions with HAU greater than 256/dose were used as the active antigenic ingredient to be used for the next emulsification procedure with adjuvants.

The immunogenic compositions of H5Con1, H5Con3, H5Con5 and H5Con5Mut were prepared into water-in-oil emulsions. In brief, water-in-oil emulsions are two phase systems consisting of a continuous oil phase and a dispersed aqueous phase whereby the aqueous phase is dispersed as small droplets in the oil phase. The oil phase used to prepare the immunogenic composition was the commercial available adjuvant MONTANIDE™ ISA 71R VG (Manufactured by Seppic Inc, Cat no: 365187), while the aqueous phase contained each of the inactivated cell culture suspensions of H5Con1, H5Con3, H5Con5 and H5Con5Mut. For each dose (0.3 ml) of the immunogenic composition, about 3 parts of aqueous phase (90 ul) were added to about 7 parts of oil phase (210 ul) and dispersed under a low-shear speed (about 11,000 rpm for 1 minute) at room temperature, and then at a high-shear speed of 16,000 rpm for 2 minutes in an iced-water bath. The Miccra disperser (Disperser machine, Cat No: Miccra D-9, Disperser head, Cat No: DS-14/P) was used to prepare the water-in-oil emulsions. For each of the immunogenic compositions of H5Con1, H5Con3, H5Con5 and H5Con5Mut, the amount of H5Con1, H5Con3, H5Con5 and H5Con5Mut was at least 256 HAU/dose.

Example 5: Cross Reactivity Tests and the Selection for H5Con1, H5Con3, H5Con5 and H5Con5Mut SPF chicken embryonated eggs were purchased from SPAFAS Jinan. After hatch, SPF chickens were randomly picked and kept in designated isolators. In the cross reactivity tests of the H5Con1, H5Con3, H5Con5 and H5Con5Mut, Re-4 to Re-8 and 03H5 (MutK+) were used to evaluate the reactivity tests of the H5Con1, H5Con3, H5Con5 and H5Con5Mut.

Re-4 to Re-8 are inactivated vaccines of the whole AIV (H5 subtype) against clades 7.2, 2.3.4, 2.3.2.1, 7.2 and 2.3.4.4, respectively, and they are commercial products from Harbin Weike Biotechnology Development Co., Ltd. 03H5 (MutK+) is Baculovirus expressed HA protein from strain A/duck/China/E319-2/03, in addition with the following changes of amino acids: S120N, D150N, S223N and additional K328 (See WO2013024113A1). The 03H5 (MutK+) was formulated into an immunogenic composition by using the same methods as the H5Con1, H5Con3, H5Con5 and H5Con5Mut.

Ten special pathogenic free (SPF) chickens at the age of 10-day old were vaccinated with one dose (0.3 ml) of the above Re-4 to Re-8 and the immunogenic compositions respectively via subcutaneous injection. The vaccinated chickens were continuously kept in the isolators. Individual chicken's serum samples were collected before vaccination, two weeks post vaccination and three weeks post vaccination. Further, serum samples prepared from a pool of the 10 chickens within the same vaccination group were tested to determine the cross HI reactivity of H5Con1, H5Con3, H5Con5 and H5Con5Mut by using a Hemaglutionation Inhibition (HI) test (See *OIE Terrestrial Manual* 2015, Chapter 2.3.4, Avian Influenza (infection with avian influenza viruses). In the HI test, the cross reactivities of H5Con1, H5Con3, H5Con5 and H5Con5Mut with 6 different clades (rBac03H5 represents clade 2.3.2, Re4 represents clade 7.2, Re5 represent clade 2.3.4, Re6 represents clade 2.3.2.1, Re1 represents clade 7.2, and Re8 represents clade 2.3.4.4.) of antigens were evaluated.

The scores of cross HI reactivity of Re-4 to Re-8, 03H5 (MutK+), H5Con1, H5Con3, H5Con5 and H5Con5Mut were shown in Table 4. In table 4, "+" represents that the number of heterologous antigens derived from different clades to which the tested sera can cross react. The sera scored with "++++" demonstrated cross reactivity with 4 different clades, the sera scored with "+++" demonstrated cross reactivity with 3 different clades, the sera scored with "++" demonstrated cross reactivity with 2 different clades, and the immune sera scored with "+" demonstrated cross reactivity with only 1 clade. The score from "+" to "++++" indicates a broader cross-reactivity. The antigens generating "++++" score were selected for the next experiments.

TABLE 4

Score of cross reactivity

| Sera generated from: | Cross HI reactivity |
|---|---|
| 03H5 (MutK+) | ++++ |
| H5Con1 | +++ |
| H5Con3 | ++++ |
| H5Con5 | n/a |
| H5Con5Mut | ++++ |
| Re-4 (clade 7.2) | ++ |
| Re-5 (clade 2.3.4) | ++++ |
| Re-6 (clade 2.3.2.1) | ++ |
| Re-7 (new clade 7.2) | + |
| Re-8 (clade 2.3.4.4) | + | n/a = non applicable

Based on the cross reactivity results, it can be determined that H5Con5Mut has a broader cross-reactivity.

Example 6: Virus Challenge and Protection Efficacy Tests

The protection efficacy of 03H5MutK+ (clade 2.3.2), H5Con3 and H5Con5Mut were further tested in this example. In the protection efficacy tests, Re6+7+8, 03H5MutK+(clade 2.3.2), H5Con3 and H5Con5Mut were evaluated. Re6+7+8 is a trivalent vaccine against clade 2.3.2.1, clade 7.2 and clade 2.3.4.4 (a mixture of Re6+Re7+Re8), and was purchased from Harbin Weike Biotechnology Development Co., Ltd. Re6+7+8 was used as a positive control vaccine for protection efficacy against each clade of challenge virus. Stocks of three different clades of Highly Pathogenic Avian Influenza (HPAI) H5Nx viruses were prepared and used for challenge trials, 1) Strain 383 (clade 2.3.2.1), 2) Strain 14079 (clade 2.3.4.4), and 3) Strain 13147 (clade 7.2). SPF chickens were vaccinated via subcutaneous route at 21-day of age with one dose (0.3 ml) of Re6+7+8, and immunogenic compositions comprising 03H5MutK+ (clade 2.3.2), H5Con3 and H5Con5Mut, each with a comparable HAU of at least 256/dose respectively. The vaccinated chickens were kept in ABSL3 (Animal Biological Safety Level 3) facilities.

Three weeks (21 days) after vaccination, chickens were challenged by nasal drop with one of the three H5Nx challenge viruses per trial. The challenge dose for each chicken was 6 $Log_{10}$ $EID50$ ($EID50$=50% of Embryo Infective doses, which means the amount of infectious virus that causes infection in the 50% of inoculated embryonated eggs). Chickens were monitored for two weeks post challenge, and mortality and morbidity of the chickens were recorded daily. Cotton swabs of tracheal and cloacal from each chicken were collected at 3, 5, and 7 days post challenge. Virus shedding was tested with the cotton swabs samples via chicken embryos based virus isolation.

The evaluation of protection efficacy against each of the challenge virus was based on the following criteria: 1) whether 100% vaccinated chickens will survive during the two weeks of monitoring period (0% mortality).

Three vaccination/challenge animal trials were conducted, and Table 5 shows the protection efficacy of Re6+7+8, 03H5MutK+ (clade 2.3.2), H5Con3 and H5Con5Mut.

TABLE 5

Protection % against each virus challenge

| Vaccination group | Protection against each challenge virus of different clades | | |
|---|---|---|---|
| | Clade 2.3.4.4 Survival % | Clade 2.3.2.1 Survival % | Clade 7.2 Survival % |
| Re6 + 7 + 8 (clades 2.3.2.1, 7.2 and 2.3.4.4) | 100% | 100% | 100% |
| 03H5MutK+ (clade 2.3.2) | 60% | N/A | N/A |
| H5Con5Mut | 100% | 100% | 100% | n/a = non applicable

It was demonstrated that the chickens vaccinated with the immunogenic composition comprising H5Con5Mut demonstrated 100% protection when challenged with HPAI viruses with the clade of 2.3.4.4, clade 2.3.2.1 and clade 7.2. That is, compared with conventional vaccines such as a mixture of Re6+Re7+Re8, the immunogenic composition comprising H5Con5Mut per se provided a superior and broader protection against three different clades of AIV at the same time.

Example 7: Protection Efficacy Tests on Different HPAI H5 Subtypes

The protection efficacy of H5Con5Mut on different HPAI H5 subtypes was further tested in this example.

The groups 1a-5a were set as immunization groups to which H5Con5Mut was administrated, and the groups 1b-5b were set as control groups to which only HPAI challenge was performed. Each group contained 12 10-day old SPF chicken. On the day of the test (D0), the chicken in groups of 1a-5a were vaccinated via subcutaneous route with one dose (0.3 ml) of the immunogenic composition comprising H5Con5Mut. After 21 days post immunization (dpi), the chicken in all groups were challenged intranasally with different HPAI H5 subtypes, and the dose of challenge was 6 $Log_{10}$ $EID_{50}$/200 ul/chicken. During 14 days post challenge, morbidity and the mortality of the chicken in each group were calculated daily.

The clinical symptoms of HAPI include insufficient spirits, rough feathers, significantly reduced appetite, coughing, secretions from the nose and eyes, swelling of the face, cyanosis, diarrhea, neurological symptoms. The appearance of at least these clinical symptoms was used for the calculation of morbidity. The mortality was calculated by counting the dead chicken. The protection % was calculated by dividing the protected chicken with the total amount of the tested chicken.

The HPAI H5 subtypes used for challenge were as follows:

| Names: | Description |
|---|---|
| SDZC | A/chicken/Shangdong/SDZC/2018 (H5N1) Clade2.3.2.1(d) |
| DK383 | A/Duck/Guangdong/383/2008 (H5N1) Clade 2.3.2.1 |
| 14079 | A/Goose/Guangdong/079/2013 (H5N1) Clade 2.3.4.4 |
| 13147 | A/Duck/Shandong/147/2013 (H5N2) Clade 7.2 |
| 17595 | A/chicken/Guangdong/17595/2017(H5N6) Clade2.3.4.4(d) |

Challenge strains were obtained from South China Agriculture University, Wushan Road, Tianhe District, Guangzhou, Guangdong Province, China, and are representative isolates of H5N1 (Clades 2.3.3.1(d) and 2.3.4.4), H5N2 (Clade 7.2) and H5N6 Clade (2.3.4.4(d)), described above.

The observed protection efficacy of H5Con5Mut against different AIV H5 subtypes was summarized in Table 6.

TABLE 6

Protection % against different HPAI H5 subtypes

| Vaccination | | Challenge | | | Clinical observation | | Protection |
|---|---|---|---|---|---|---|---|
| Group | Vaccination | strain | day | dose | morbidity | mortality | % |
| 1a | H5Con5Mut | SDZC | 21 dpi | 6$Log_{10}EID_{50}$/200 ul/chicken | 0/12 | 0/12 | 100% |
| 1b | None | SDZC | | | 12/12 | 12/12 | 0 |

TABLE 6-continued

Protection % against different HPAI H5 subtypes

| | | | | | Clinical observation | | |
|---|---|---|---|---|---|---|---|
| | Vaccination | Challenge | | | | | Protection |
| Group | Vaccination | strain | day | dose | morbidity | mortality | % |
| 2a | H5Con5Mut | DK383 | | | 0/12 | 0/12 | 100% |
| 2b | None | DK383 | | | 12/12 | 12/12 | 0 |
| 3a | H5Con5Mut | 14079 | | | 0/12 | 0/12 | 100% |
| 3b | None | 14079 | | | 12/12 | 12/12 | 0 |
| 4a | H5Con5Mut | 13147 | | | 0/12 | 0/12 | 100% |
| 4b | None | 13147 | | | 12/12 | 12/12 | 0 |
| 5a | H5Con5Mut | 17595 | | | 0/12 | 0/12 | 100% |
| 5b | None | 17595 | | | 12/12 | 12/12 | 0 |

Table 6 showed that in each control group, the challenge on 21 dpi was valid because a mortality of 100% was observed during the 14 weeks post challenge, and H5Con5Mut demonstrated 100% protection when the chicken were challenged with H5N1, H5N2 and H5N6. The data demonstrated that H5Con5Mut provided superior and broader protection efficacy against different HPAI H5 subtypes.

Example 8: Protection Onset Tests of H5Con5Mut

The protection onset of H5Con5Mut against HPAI challenge was further tested in this example.

The groups 1a and 2a were set as immunization groups to which H5Con5Mut was administered, and the groups 1b and 2b were set as control groups to which only HPAI challenge (14079 strain) was performed. Each group contained 12 10-day old SPF chicken, and the experiments were repeated twice. On the day of the test (D0), the chicken in groups 1a and 2a were vaccinated via subcutaneous route with one dose (0.3 ml) of the immunogenic composition comprising H5Con5Mut. After 7 days post immunization (dpi), the chicken in groups of 1a and 1b were challenged intranasally with the 14079 strain. After 14 days post immunization (dpi), the chicken in groups of 2a and 2b were challenged intranasally with the 14079 strain. The dose of challenge was 6 $Log_{10}$ $EID_{50}$/200 ul/chicken. During 14 days post challenge, the morbidity and the mortality of the chicken in each group were calculated daily. The observed protection onset of H5Con5Mut was summarized in Table 7.

Table 7 demonstrated that H5Con5Mut induced a protection as early as 7 dpi, with a 100% protection at 14 dpi. The data demonstrated that H5Con5Mut provided a quick and early onset protection against HPAI challenge.

Example 9: Protection Duration Tests of H5Con5Mut

The protection duration of H5Con5Mut against HPAI challenge was further tested in this example.

The groups 1-3 were set as immunization groups to which H5Con5Mut was administered, and the group 4 was set as control groups to which only HPAI challenge (14079 strain) was performed. Each group contained 12 10-day old SPF chicken, and the experiments were performed twice. On the day of the test (D0), the chicken in groups 1-3 were vaccinated via subcutaneous route with one dose (0.3 ml) of the immunogenic composition comprising H5Con5Mut. After 28 dpi, 35 dpi and 42 dpi, the chicken in groups 1-3 were challenged intranasally with the 14079 strain respectively. In the control group, the chicken were challenged intranasally with the 14079 strain after 28 dpi. The dose of challenge was 6 $Log_{10}$ $EID_{50}$/200 ul/chicken. During 14 days post challenge, the morbidity and the mortality of the chicken in each group were calculated daily. The observed protection duration of H5Con5Mut was summarized in Table 8.

TABLE 7

Protection onset of H5Con5Mut against HPAI challenge

| | | | | | Clinical observation | | |
|---|---|---|---|---|---|---|---|
| | Vaccination | Challenge | | | | | Protection |
| Group | Vaccination | strain | day | dose | morbidity | mortality | % |
| 1a | H5Con5Mut | 14079 | 7 dpi | 6$Log_{10}EID_{50}$/200 ul/chicken | 6/12 | 6/12 | 50% |
| 1b | None | | 7 dpi | | 12/12 | 12/12 | 0 |
| 2a | H5Con5Mut | | 14 dpi | | 0/12 | 0/12 | 100% |
| 2b | None | | 14 dpi | | 12/12 | 12/12 | 0 |

TABLE 8

Protection duration of H5Con5Mut against HPAI challenge

| | Vaccination | Challenge | | | Clinical observation | | Protection |
|---|---|---|---|---|---|---|---|
| Group | Vaccination | strain | day | dose | morbidity | mortality | % |
| 1 | H5Con5Mut | 14079 | 28 dpi | 6Log10EID$_{50}$/200 ul/chicken | 0/12 | 0/12 | 100% |
| 2 | H5Con5Mut | | 35 dpi | | 0/12 | 0/12 | 100% |
| 3 | H5Con5Mut | | 42 dpi | | 0/12 | 0/12 | 100% |
| 4 | None | | 28 dpi | | 12/12 | 12/12 | 0 |

Table 8 showed that H5Con5Mut provided 100% protection lasting for at least 42 dpi. The data demonstrated that H5Con5Mut provided a long-lasting and effective protection against HPAI challenge.

Example 10: Protection Test on Chicken with Different Days of Age

The protection of H5Con5Mut on chicken with different days of age against HPAI challenge was further tested in this example.

The groups 1-2 were set as immunization groups to which H5Con5Mut was administrated, and the group 3 was set as a control group to which only HPAI challenge (14079 strain) was performed. Each group contained 12 SPF chicken, and the experiments were performed twice. In group 1, the chicken with 1 day old were vaccinated via subcutaneous route with one dose (0.3 ml) of the immunogenic composition comprising H5Con5Mut. In group 2, the chicken with 10 days old were vaccinated via subcutaneous route with one dose (0.3 ml) of the immunogenic composition comprising H5Con5Mut. After 21 dpi, the chicken in groups 1-3 were challenged intranasally with the 14079 strain respectively. The dose of challenge was 6 Log$_{10}$ EID$_{50}$/200 ul/chicken. During 14 days post challenge, the morbidity and the mortality of the chicken in each group were calculated daily. The observed protection of H5Con5Mut on chicken with different days of age was summarized in Table 9.

Table 9 showed that H5Con5Mut provided 100% protection to 1 day old chicken against HPAI challenge. The data demonstrated that H5Con5Mut provided a superior protection on chicken even from newborns.

Example 11: Protection Test of Different Routes of Administration

The protection of H5Con5Mut on chicken via different routes of administration was further tested in this example.

The groups 1-2 were set as immunization groups to which H5Con5Mut was administrated, and the group 3 was set as control groups to which only HPAI challenge (14079 strain) was performed. Each group contained 12 10-day old SPF chicken, and the experiments were performed twice. On the day of the test (D0), the chicken in groups 1-2 were vaccinated via subcutaneous route with one dose (0.3 ml) of the immunogenic composition comprising H5Con5Mut via subcutaneous (S.C.) or intramuscular (I.M.) administration. After 21 dpi, the chicken in groups 1-3 were challenged intranasally with the 14079 strain respectively. The dose of challenge was 6 Log 10EID$_{50}$/200 ul/chicken. During 14 days post challenge, the morbidity and the mortality of the chicken in each group were calculated daily. The observed protection of H5Con5Mut on chicken via different routes of administration was summarized in Table 10.

TABLE 9

Protection of H5Con5Mut on chicken with different days of age

| | Vaccination | | Challenge | | | Clinical observation | | Protection |
|---|---|---|---|---|---|---|---|---|
| Group | Vaccination | Age | strain | day | dose | morbidity | mortality | % |
| 1 | H5Con5Mut | 1 d | 14079 | 21 dpi | 6Log10EID$_{50}$/200 ul/chicken | 0/12 | 0/12 | 100% |
| 2 | H5Con5Mut | 10 d | | | | 0/12 | 0/12 | 100% |
| 3 | None | | | | | 12/12 | 12/12 | 0 |

TABLE 10

Protection of H5Con5Mut on chicken via different routes of administration

| | Vaccination | | | Challenge | | | Clinical observation | | Protection |
|---|---|---|---|---|---|---|---|---|---|
| Group | Vaccination | Age | Route | strain | day | dose | morbidity | mortality | % |
| 1 | H5Con5Mut | 10 d | S.C. | 14079 | 21 dpi | 6Log$_{10}$EID$_{50}$/200 ul/ chicken | 0/12 | 0/12 | 100% |
| 2 | H5Con5Mut | 10 d | I.M. | | | | 0/12 | 0/12 | 100% |
| 3 | None | | | | | | 12/12 | 12/12 | 0 |

Table 10 showed that H5Con5Mut provided superior protection on chicken via both S.C. and I.M. administrations, and the protection efficacy of H5Con5Mut was not limited to a certain route of administration. The flexible way of administration allowed H5Con5Mut to be suitable for chicken at different growth status such as newborns with little muscle.

All of the compositions and methods disclosed and claimed herein can be made and executed without undue experimentation in light of the present disclosure. While the compositions and methods of this invention have been described in terms of exemplified embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The invention claimed is:

1. An immunogenic composition comprising a hemagglutinin protein of avian influenza virus H5 subtype, where in the hemagglutinin protein comprises:
   (a) an the amino acid sequence as set forth in SEQ ID NO: 6; or
   (b) an the amino acid sequence as set forth in SEQ ID NO: 5.

2. The immunogenic composition of claim 1, wherein the hemagglutinin protein is contained in a cell culture, and the cell culture is prepared by culturing cells containing an expression vector capable of expressing the hemagglutinin protein as defined in claim 1.

3. The immunogenic composition of claim 2, wherein the expression vector encodes a the nucleic acid molecule as set forth in SEQ ID NO: 10 or SEQ ID NO: 11.

4. The immunogenic composition of claim 2, wherein the expression vector is a baculovirus, and the cells are insect cells.

5. The immunogenic composition of claim 2, wherein the cell culture is subjected to an inactivation step.

6. The immunogenic composition of claim 2, wherein the immunogenic composition comprises a portion or all of the cell culture.

7. The immunogenic composition of claim 1, wherein the immunogenic composition further comprises an adjuvant.

8. The immunogenic composition of claim 7, wherein the adjuvant is a water-in-oil emulsion.

9. The immunogenic composition of claim 1, wherein the immunogenic composition is administered in a single-dose administration or multiple doses administration; and/or the immunogenic composition is administered subcutaneously or intramuscularly; and and/or the immunogenic composition is to be administered to an animal at 1 day of age or older, at 7 days of age or older, at 10 days of age or older, at 15 days of age or older, or at 21 days of age or older.

10. The immunogenic composition of claim 2, wherein the immunogenic composition further comprises an adjuvant.

11. The immunogenic composition of claim 10, wherein the adjuvant is a water-in-oil emulsion.

12. The immunogenic composition of claim 3, wherein the expression vector is a baculovirus, and the cells are insect cells.

13. The immunogenic composition of claim 3, wherein the cell culture is subjected to an inactivation step.

14. The immunogenic composition of claim 3, wherein the immunogenic composition comprises a portion or all of the cell culture.

15. The immunogenic composition of claim 1, wherein the immunogenic composition is administered in a single-dose administration or multiple doses administration; and/or the immunogenic composition is to be administered to an animal at 1 day of age or older, at 7 days of age or older, at 10 days of age or older, at 15 days of age or older, or at 21 days of age or older.

16. The immunogenic composition of claim 1, wherein the hemagglutinin protein comprises the amino acid sequence as set forth in SEQ ID NO: 5.

17. The immunogenic composition of claim 1, wherein the hemagglutinin protein comprises the amino acid sequence as set forth in SEQ ID NO: 6.

18. The immunogenic composition of claim 5, wherein the inactivation step uses binary ethyleneimine.

19. The immunogenic composition of claim 13, wherein the inactivation step uses binary ethyleneimine.

\* \* \* \* \*